United States Patent
Kayser et al.

(10) Patent No.: US 11,674,126 B2
(45) Date of Patent: Jun. 13, 2023

(54) BIOTECHNOLOGICAL PRODUCTION OF CANNABINOIDS

(71) Applicant: Technische Universitaet Dortmund, Dortmund (DE)

(72) Inventors: Oliver Kayser, Dortmund (DE); Felix-Oliver Stehle, Witten (DE)

(73) Assignee: Technische Universitaet Dortmund, Dortmund (DE)

(*) Notice: Subject to any disclaimer, the term of this patent is extended or adjusted under 35 U.S.C. 154(b) by 0 days.

(21) Appl. No.: 17/257,867

(22) PCT Filed: Jul. 17, 2019

(86) PCT No.: PCT/EP2019/069223
§ 371 (c)(1),
(2) Date: Jan. 5, 2021

(87) PCT Pub. No.: WO2020/016287
PCT Pub. Date: Jan. 23, 2020

(65) Prior Publication Data
US 2021/0292799 A1    Sep. 23, 2021

(30) Foreign Application Priority Data
Jul. 17, 2018    (DE) .................... 10 2018 117 233.8

(51) Int. Cl.
*C12N 9/10*    (2006.01)
*C12P 7/42*    (2006.01)

(52) U.S. Cl.
CPC .............. *C12N 9/1085* (2013.01); *C12P 7/42* (2013.01); *C12Y 205/01* (2013.01)

(58) Field of Classification Search
CPC ................................ C12N 9/1085; C12P 7/42
See application file for complete search history.

(56) References Cited

U.S. PATENT DOCUMENTS

| | | | |
|---|---|---|---|
| 10,894,952 B2* | 1/2021 | Mendez | C12N 9/1085 |
| 11,149,291 B2* | 10/2021 | Mikheev | C12Y 205/01001 |
| 2016/0010126 A1* | 1/2016 | Poulos | C12N 9/1029 |
| | | | 435/125 |

FOREIGN PATENT DOCUMENTS

| | | |
|---|---|---|
| DE | 102010011601 A1 | 9/2011 |
| WO | 2006081537 A2 | 8/2006 |
| WO | 2011017798 A1 | 2/2011 |
| WO | 2016010827 A1 | 1/2016 |
| WO | 2019071000 A1 | 4/2019 |
| WO | 2019173770 A1 | 9/2019 |

OTHER PUBLICATIONS

Brown. A0A0N1NUQ7_9ACTN. UnitProtKB/TrEMBL. Jun. 7, 2017.*
Studer. Residue mutations and their impact on protein structure and function: detecting beneficial and pathogenic changes. Biochem. J. (2013) 449, 581-594.*
Stout. The hexanoyl-CoA precursor for cannabinoid biosynthesis is formed by an acyl-activating enzyme in Cannabis sativa trichomes. Plant J. 71:353-365(2012).*
Zirpel et al., "Engineering yeasts as platform organisms for cannabinoid biosynthesis", Journal of Biotechnology, 2017, pp. 204-212, vol. 259, Elsevier B.V.
Valliere et al., "A cell-free platform for the prenylation of natural products and application to cannabinoid production", Nature Communications, 2019, pp. 1-9.
Search report from parallel German Patent Application 10 2018 117 233.8 dated Mar. 7, 2019, 7 pages (for reference purposes only).
International search report from parallel PCT Patent Application PCT/EP2019/069223 dated Oct. 25, 2019, 13 pages (for reference purposes only).

* cited by examiner

*Primary Examiner* — Yong D Pak
(74) *Attorney, Agent, or Firm* — Viering Jentschura & Partner Mbb

(57) ABSTRACT

A method for the recombinant production of cannabigerolic acid in a host organism may use a modified prenyltransferase. A modified prenyltransferase, a nucleic acid molecule that codes for the modified prenyltransferase, and a recombinant organism that includes the modified prenyltransferase and/or the nucleic acid are also disclosed here.

12 Claims, 1 Drawing Sheet
Specification includes a Sequence Listing.

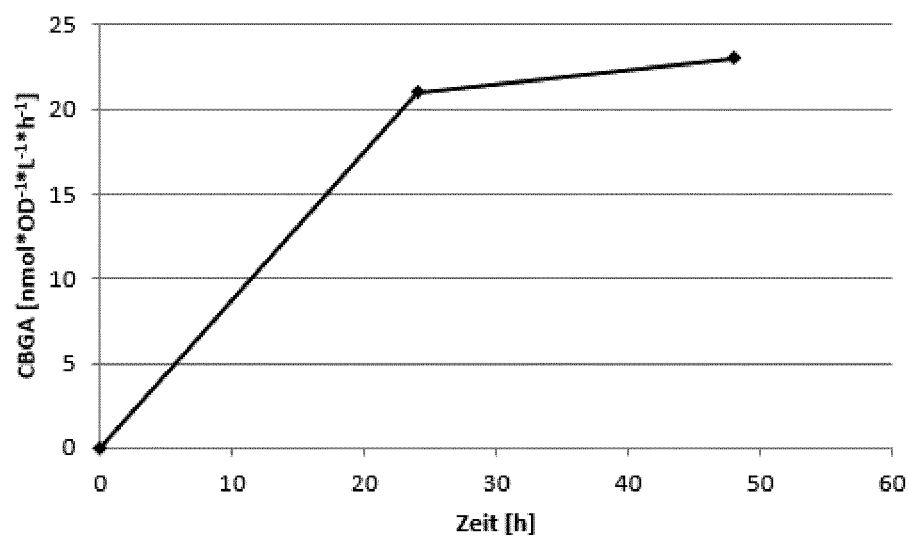

BIOTECHNOLOGICAL PRODUCTION OF CANNABINOIDS

CROSS-REFERENCE TO RELATED APPLICATIONS

The present application is a national stage entry according to 35 U.S.C. § 371 of PCT application No.: PCT/EP2019/069223 filed on Jul. 17, 2019; which claims priority to German Patent Application Serial No.: 10 2018 117 233.8 filed on Jul. 17, 2018; all of which are incorporated herein by reference in their entirety and for all purposes.

REFERENCE TO A SEQUENCE LISTING SUBMITTED VIA EFS-WEB

The content of the ASCII text file of the sequence listing named "P79816US_seq_ST25", which is 113 kb in size was created on Jul. 17, 2018 and electronically submitted via EFS-Web herewith the application is incorporated by reference in its entirety.

TECHNICAL FIELD

The present disclosure relates to a method for recombinant production of cannabigerolic acid in a host organism with the aid of a modified prenyltransferase. The disclosure further relates to a modified prenyltransferase, a nucleic acid molecule which encodes such a modified prenyltransferase, and a recombinant organism which comprises the modified prenyltransferase and/or the nucleic acid molecule.

BACKGROUND

Cannabinoids and their derivatives are currently experiencing increased interest as active ingredients and drugs, or as starting materials for further syntheses. The increased interest is associated, for example, with the progressive legalization of cannabinoids for medical use.

Cannabinoids occur, for example, in humans in the form of endocannabinoids (*cannabis*-like substances). But they are mainly known as phytocannabinoids from plants, especially from the plant *Cannabis sativa* L., also known as *Cannabis* or marijuana.

In the human body, cannabinoids act on specific cannabinoid receptors, for example G-protein-coupled receptors, and other target molecules and thereby cause, for example, the release of neurotransmitters or an activation of postsynaptic calcium channels. This means that they may be involved in a multiplicity of body and metabolic functions.

Tetrahydrocannabinol (THC) in particular is commonly used as a therapeutic agent in the treatment of chemotherapy-associated nausea and emesis, AIDS-related loss of appetite and in the case of pain or muscle spasms in multiple sclerosis. The cannabinoid cannabidiol (CBD) is being considered as a candidate active ingredient for epilepsy and psoriasis. The soporific and anticonvulsant effect of cannabinol (CBN) and the anti-inflammatory or else antidepressant effect of cannabichromenes (CBC) are currently being investigated.

To date, cannabinoids have mostly been made available by extraction from plants or by means of chemical synthesis. Successful extraction is often inadequate because cannabinoids are only present in low concentrations in plants. They occur especially in the leaves or the flower bud. After extraction, what is usually present is a mixture of different cannabinoids. The purification of an individual substance is complex and expensive and often results in inadequate results.

The chemical synthesis of such compounds also has many disadvantages, such as, for example, the complex and cost-intensive purification of intermediates after individual synthesis steps, the use of harmful solvents and chemicals, and the absent or only inadequate regiospecificity or stereospecificity.

The poor availability makes medical research with cannabinoids difficult.

One of the most common forms of administration of cannabinoids continues to be smoking. However, it is known that non-smoking patients in particular prefer an alternative form of administration.

For the reasons mentioned above, the biotechnological synthesis of cannabinoids is becoming increasingly important.

U.S. Pat. No. 8,884,100 B2 provides a detailed description of the cannabigerolic acid synthase from the plant *Cannabis sativa* L., an aromatic prenyltransferase which is responsible for the synthesis of cannabigerolic acid and other products.

US patent US 2016/0010126 A1 (WO 2016/010827 A1) discloses, for example, the synthesis of different cannabinoids in yeast cells.

However, the successful biotechnological production of cannabinoids has failed to date because of the inadequate reaction of individual biosynthesis steps. Therefore, there continues to be a need for alternative synthesis pathways and enzymes for producing individual cannabinoids and their precursors in larger quantities as purely as possible.

SUMMARY

Surprisingly, by modifying an aromatic prenyltransferase (NphB) from *Streptomyces* sp. CL190 (Zirpel et al., J. Biotechnol., 2017, 259, 204-212), the inventors have found a way to extend the substrate specificity of the enzyme to the substrate olivetolic acid and, at the same time, to increase the product specificity of the enzyme for cannabigerolic acid. In contrast to the modified variant, the wild-type enzyme NphB produces 2-O-geranyl olivetolic acid to a substantial extent and the desired product cannabigerolic acid only to a small extent.

Cannabigerolic acid is produced recombinantly by introducing the gene which encodes the modified NphB variant into a host organism and expressing it. In addition, further synthesis pathways and enzymes of the host organism can be optimized in order to allow improved recombinant cannabigerolic acid synthesis in the host organism. Cannabigerolic acid is an important precursor of many other cannabinoids, such as, for example, $\Delta^9$-tetrahydrocannabinolic acid, and the improved synthesis of cannabigerolic acid thus forms the basis of the biosynthesis of subsequent cannabinoids.

In a first aspect, a method for recombinant production of cannabigerolic acid in a host organism may include a) introducing into the host organism a nucleic acid molecule which comprises a first, heterologous nucleotide sequence which encodes a modified prenyltransferase, the prenyltransferase being modified in such a way that (1) the substrate specificity is extended to olivetolic acid and (2) upon reaction of olivetolic acid with geranyl diphosphate the product ratio of cannabigerolic acid:2-O-geranyl olivetolic acid is at least 1:1, preferably at least 5:1;

b) culturing the host organism under conditions which allow the expression of the nucleotide sequence which encodes the prenyltransferase;

c) culturing the host organism under conditions which allow the production of cannabigerolic acid.

In a second aspect, a modified prenyltransferase, which may have an amino acid sequence which has at least 80%, preferably at least 81%, 82%, 83%, 84%, 85%, 86%, 87%, 88%, 89%, 90%, 91%, 92%, 93%, 94%, 95%, 95.5%, 96.0%, 96.5%, 97.0%, 97.2%, 97.4%, 97.6%, 97.8% 98.0%, 98.2%, 98.4%, 98.6%, 98.8%, 99.0%, 99.1%, 99.2%, 99.3%, 99.4% or 99.5%, sequence identity with the amino acid sequence specified in SEQ ID NO: 2 over the entire length thereof and is modified in such a way that it has at least one amino acid substitution with respect to the amino acid sequence specified in SEQ ID NO: 2, preferably a substitution at at least one of the positions corresponding to positions 126, 161, 162, 175, 213 or 295 in SEQ ID NO: 2. In various embodiments, said modified prenyltransferase has substrate specificity for olivetolic acid and can react it with geranyl diphosphate in such a way that the product ratio of cannabigerolic acid:2-O-geranyl olivetolic acid is at least 1:1, preferably at least 5:1. The specified product ratio is preferably based on the molar product ratio. Unless otherwise stated, the ratios specified herein are therefore always based on molar ratios.

In a further aspect, a nucleic acid molecule may include a nucleotide sequence which encodes the modified prenyltransferase.

Finally, in a further aspect, a recombinant organism may include at least one prenyltransferase and/or at least one nucleic acid.

DETAILED DESCRIPTION

"At least one", as used herein, refers to 1 or more, for example 2, 3, 4, 5, 6, 7, 8, 9 or more. This information does not refer to the absolute amount of a feature or component, but to the type of the feature or component. "At least one further heterologous nucleic acid" therefore means, for example, one or more further heterologous nucleic acids that are different. Together with specified amounts, the specified amounts refer to the total amount of the correspondingly designated type of component.

Numerical values specified herein without decimal places refer in each case to the full specified value with one decimal place. For example, "99%" stands for "99.0%".

The expressions "approximately" or "about" in connection with a numerical value refer to a variance of ±10%, based on the specified numerical value, preferably ±5%, particularly preferably ±1%.

The terms "heterologous" or "recombinant" are used herein to indicate that the corresponding molecule does not occur naturally in the host organism. The heterologous or recombinant expression of one or more nucleotide sequence(s) in a host organism thus means that said host organism does not contain or express said nucleotide sequence(s) under natural conditions. This means that, in the host organism, it is possible to produce heterologous or recombinant proteins which would not be produced in the host organism under natural conditions. The nucleotide sequences introduced into the host organism can be wild-type sequences and/or modified sequences from another organism. In addition, the host cell can be altered/mutated in such a way that the expression of host genes or host nucleotide sequences is downregulated or switched off. The associated host proteins or associated functions of the downregulated or switched-off host genes can be replaced, altered, attenuated or boosted by the heterologously produced protein. Promoter sequences in the host organism can be modified, too, or activators or repressors can be introduced into the nucleotide sequence, the host genome or the expression vector in order to regulate the expression of the heterologous or recombinant nucleotide sequence.

"Modified" or "modification", based on a nucleotide sequence or amino acid sequence or on a nucleic acid or protein/enzyme, means that the corresponding sequence is modified proceeding from the naturally occurring sequence (wild type), with the result that it is distinguishable therefrom. In particular, the modification is that a sequence can be mutated, for example by substitution, deletion or insertion.

The identity of nucleotide or amino acid sequences is determined by a sequence comparison. Said sequence comparison is based on the BLAST algorithm which is established in the prior art and commonly used (cf. for example Altschul, S. F., Gish, W., Miller, W., Myers, E. W. & Lipman, D. J. (1990) "Basic local alignment search tool." J. Mol. Biol. 215: 403-410, and Altschul, Stephan F., Thomas L. Madden, Alejandro A. Schaffer, Jinghui Zhang, Hheng Zhang, Webb Miller, and David J. Lipman (1997): "Gapped BLAST and PSI-BLAST: a new generation of protein database search programs"; Nucleic Acids Res., 25, pages 3389-3402) and is done in principle by assigning similar orders of nucleotides or amino acids in the nucleotide or amino acid sequences to one another. A tabular assignment of the relevant positions is referred to as an alignment. Another algorithm available in the prior art is the FASTA algorithm. Sequence comparisons (alignments), especially multiple sequence comparisons, are created using computer programs. What are commonly used are, for example, the Clustal series, T-Coffee or programs based on these programs or algorithms. Sequence comparisons (alignments) are also possible using the computer program Vector NTI® Suite 10.3 (Invitrogen Corporation, 1600 Faraday Avenue, Carlsbad, Calif., USA) with the specified standard parameters, the AlignX module of which for sequence comparisons is based on ClustalW. Unless otherwise stated, the sequence identity specified herein is determined using the BLAST algorithm.

Such a comparison also makes it possible to state the similarity of the compared sequences in relation to one another. It is usually specified in terms of percent (sequence) identity, i.e., the proportion of identical nucleotides or amino acid residues at the same positions or positions corresponding to one another in an alignment. This means, for example, that amino acid sequences with a sequence identity of less than 100% are typically amino acid sequences in which one or more amino acids have been modified, for example added, removed, exchanged or modified in some other way, compared to an amino acid sequence serving as a reference. The broader term of homology includes conserved amino acid exchanges in amino acid sequences, i.e., amino acids having similar chemical activity, since they usually exercise similar chemical activities within the protein. Therefore, the similarity of the compared sequences can also be specified as percent homology or percent similarity. Identities and/or homologies can be specified over entire polypeptides or genes or only over individual regions. Homologous or identical regions of different nucleotide or amino acid sequences are therefore defined by matches in the sequences. Such regions often have identical functions. They can be small and comprise only a few nucleotides or amino acids. Such small regions often exercise essential functions for the overall activity of the protein. It may therefore be meaningful to base sequence matches only on individual, possibly small, regions. Unless otherwise stated, specified sequence identities or homologies in the present application are, however, based on the total length of the nucleotide or amino acid sequence specified in each case. This means, for example, that if a reference sequence has a length of 100 amino acids, each sequence to be compared having a sequence identity of, for example, 80% must have at least 80 identical amino acids at corresponding positions of the reference of 100 amino acids when both sequences are directly compared. Said 80 amino acids can be contiguous or noncontiguous. This means that the sequence to be compared must have at least a length of 80 amino acids. The remaining 20 amino acids can differ in the two sequences. A comparable definition of "sequence identity" can be applied to nucleotide sequences. Here, the term "identity" refers to identical nucleotides at corresponding positions.

The above-described and further aspects, embodiments, features and advantages will become apparent to a person skilled in the art from studying the following detailed description and claims. In addition, any feature from one embodiment can be introduced into any other embodiment. Furthermore, it is self-evident that the examples contained herein are intended to describe and illustrate the non-limiting embodiments, but do not restrict them, and the non-limiting embodiments are especially not restricted to said examples.

The below-presented facts, subjects and embodiments which are described for the method are also applicable to all other subjects of the embodiments, such as the prenyltransferase, the nucleic acid molecule and/or the recombinant organism.

The first aspect relates to a method for recombinant production of cannabigerolic acid in a host organism, the method comprising:

a) introducing into the host organism a nucleic acid molecule which comprises a first, heterologous nucleotide sequence which encodes a modified prenyltransferase, wherein the prenyltransferase is modified in such a way that (1) the substrate specificity is extended to olivetolic acid and (2) upon reaction of olivetolic acid with geranyl diphosphate the product ratio of cannabigerolic acid:2-O-geranyl olivetolic acid is at least 1:1, preferably at least 5:1;

b) culturing the host organism under conditions which allow the expression of the nucleotide sequence which encodes the modified prenyltransferase;

c) culturing the host organism under conditions which allow the production of cannabigerolic acid.

The specified product ratio is preferably based on the molar product ratio.

All cells, i.e., prokaryotic and eukaryotic cells, are suitable in principle as host organism. These can be mammalian cells (such as, for instance, cells from humans), other animal cells (e.g., insect cells), plant cells or microorganisms such as yeasts, fungi or bacteria.

Preference is given to those host cells which can advantageously be handled using gene technology, for example with regard to the transformation with the nucleic acid or the vector and the stable establishment thereof. Furthermore, preferred host cells are distinguished by good microbiological and biotechnological manageability. This concerns, for example, easy culturability, high growth rates, low demands on fermentation media, and good production and secretion rates for foreign proteins. Furthermore, the proteins can be modified by the cells which produce them after production thereof, for example by attachment of sugar molecules, formylations, aminations, etc. Such post-translational modifications can functionally influence the enzymes.

Unicellular fungi, yeasts or bacteria are particularly preferred herein, most preferably yeasts. They are distinguished by short generation times and low demands on the culturing conditions. Cost-effective culturing processes or production processes can be established as a result. In addition, a person skilled in the art has a wealth of experience with unicellular fungi, yeasts or bacteria in fermentation technology.

Particularly suitable bacteria, yeasts or unicellular fungi are those bacteria, yeasts or unicellular fungi which are deposited as bacterial, yeast or fungal strains at the German Collection of Microorganisms and Cell Cultures GmbH (DSMZ), Braunschweig, Germany. Unicellular fungi, yeasts and bacteria which are suitable belong to the genera which are present in the catalogs of the Leibniz Institute DSMZ-German Collection of Microorganisms and Cell Cultures GmbH under http://www.dsmz.de.

Cells preferred are those of the genera *Aspergillus, Corynebacterium, Brevibacterium, Bacillus, Acinetobacter, Alcaligenes, Actinobacillus, Anaerobiospirillum, Basfia, Wollinella, Fibrobacter, Ruminococcus, Mannheimia, Lactobacillus, Lactococcus, Paracoccus, Lactococcus, Candida, Pichia* (also called *Komagataella*), *Hansenula, Kluyveromyces, Saccharomyces, Escherichia, Zymomonas, Yarrowia, Methylobacterium, Ralstonia, Pseudomonas, Rhodospirillum, Rhodobacter, Burkholderia, Clostridium* or *Cupriavidus*, particular preference being given to *Aspergillus nidulans, Aspergillus niger, Alcaligenes latus, Bacillus megaterium, Bacillus subtilis, Brevibacterium flavum, Brevibacterium lactofermentum, Escherichia coli, Basfia succiniciproducens, Wollinella succinogenes, Fibrobacter succinogenes, Ruminococcus flavefaciens, Anaerobiospirillum succiniciproducens, Mannheimia succiniciproducens, Actinobacillus succinogenes, Saccharomyces cerevisiae, Kluyveromyces lactis, Kluyveromyces marxianus, Candida blankii, Candida rugosa, Corynebacterium glutamicum, Corynebacterium efficiens, Zymonomas mobilis, Yarrowia lipolytica, Methylobacterium extorquens, Hansenula polymorpha, Ralstonia eutropha, Rhodobacter sphaeroides, Paracoccus versutus, Pseudomonas aeruginosa, Acinetobacter calcoaceticus, Pichia pastoris* (also called *Komagataella phaffii*), *Thermoanaerobacter kivui, Acetobacterium woodii, Acetoanaerobium notera, Clostridium aceticum, Butyribacterium methylotrophicum, Clostridium acetobutylicum, Clostridium saccharoperbutylacetonicum, Clostridium beijerinckii, Clostridium butyricum, Moorella thermoacetica, Eubacterium limosum, Peptostreptococcus productus, Clostridium ljungdahlii, Clostridium carboxidivorans, Clostridium scatalogenes, Rhodospirillum rubrum, Burkholderia thailandensis* and *Pseudomonas putida*.

In preferred embodiments, the host organism is a yeast, preferably *Saccharomyces cerevisiae, Kluyveromyces marxianus, Yarrowia lipolytica* or *Pichia pastoris*, further preferably *Saccharomyces cerevisiae* or *Pichia pastoris*, especially *Saccharomyces cerevisiae*.

Host cells can be altered with respect to their requirements for the culture conditions, can have different or additional selection markers or can also express other or additional proteins. The host cells can especially also be those which express multiple proteins or enzymes recombinantly.

In a preferred embodiment, the nucleotide sequence which encodes the modified prenyltransferase is codon-harmonized for expression in the host organism, preferably *Saccharomyces cerevisiae, Kluyveromyces marxianus, Yar-* rowia lipolytica or Pichia pastoris, further preferably Saccharomyces cerevisiae or Pichia pastoris, especially Saccharomyces cerevisiae.

In a further preferred embodiment, the nucleotide sequence which encodes the modified prenyltransferase is
(1) derived from the NphB gene from the Streptomyces sp. strain CL190; and/or
(2) codon-harmonized for expression in the host organism.

The NphB gene from Streptomyces sp. CL190 encodes an aromatic prenyltransferase and preferably has the nucleotide sequence specified in SEQ ID NO: 1. The enzyme is originally involved in naphterpin biosynthesis in Streptomyces sp.

The wild-type prenyltransferase can react the substrates olivetolic acid and geranyl diphosphate by means of a C-C Friedel-Crafts alkylation to form 2-O-geranyl olivetolic acid and cannabigerolic acid. However, what are synthesized in this case are 2-O-geranyl olivetolic acid to a substantial extent and cannabigerolic acid only in a small amount.

In the context of this application, "wild type" refers to, for example, a cell, the genome of which is present in a state as has arisen naturally by evolution. The term is used both for the entire cell and for individual genes. Therefore, the term "wild type" especially does not cover those cells or those genes, the gene sequences of which have been altered at least in part by humans by means of recombinant/gene-technology methods.

A nucleic acid molecule which comprises a first heterologous nucleotide sequence which encodes a modified prenyltransferase is introduced into the host organism and expressed, the result being that the reaction of olivetolic acid and geranyl diphosphate to form cannabigerolic acid (and optionally also 2-O-geranyl olivetolic acid) is made possible and cannabigerolic acid and 2-O-geranyl olivetolic acid are produced at least in a ratio of 1:1, preferably at least in a ratio of 5:1, further preferably at least in a ratio of 10:1, especially at least in a ratio of 15:1, further preferably at least in a ratio of 20:1. The ratio is preferably a molar ratio.

The cannabigerolic acid synthesis is achieved by the host organism producing the prenyltransferase which is modified and which is encoded by the first heterologous nucleotide sequence. The nucleotide sequence is preferably based on the nucleotide sequence according to SEQ ID NO: 1, but is modified in such a way that it encodes the modified prenyltransferase.

In addition, further heterologous nucleotide sequences can be introduced into the host organism and/or one or more host enzymes can be present in a modified or optimized form in order to improve the reaction of individual synthesis steps or to provide substrates. In this connection, the modification or optimization of the enzymes can be based on a gene mutation of the associated nucleotide sequence, preferably on deletion(s), insertion(s) and/or nucleotide exchange(s) of one or more nucleotides, of one or more codons, or of gene segments. The further heterologous sequences, together with the first heterologous sequence which encodes the modified prenyltransferase, can be comprised by a single nucleic acid molecule, for example a plasmid, or be contained on multiple separate nucleic acid molecules.

The heterologous nucleotide sequences which encode proteins foreign to the host, especially the modified prenyltransferase, can be codon-harmonized or codon-optimized, especially codon-harmonized.

Since a certain amino acid sequence can be encoded by multiple different nucleic acids because of the degeneracy of the genetic code, all nucleotide sequences which can encode the proteins described herein, especially the modified prenyltransferases, may be useful herein. A person skilled in the art is capable of determining said nucleotide sequences unequivocally because, despite the degeneracy of the genetic code, defined amino acids must be assigned to individual codons. Proceeding from an amino acid sequence, a person skilled in the art can therefore ascertain without any problems nucleic acids encoding said amino acid sequence. Furthermore, in the case of nucleic acids, it is possible, with respect to the wild-type or starting sequence, to replace one or more codons with synonymous codons (i.e., encoding the same amino acid). This aspect relates especially to the heterologous expression of the nucleic acids. Since every organism, for example a host cell of a production strain, has a defined codon usage, a codon in a given organism may be translated less efficiently than a synonymous codon encoding the same amino acid.

"Codon optimization" of a nucleotide sequence is therefore preferably associated with a complete adaptation of the original nucleotide sequence to commonly used codons of the host organism. By contrast, "codon-harmonized" preferably describes an adaptation of the nucleotide sequence to the host organism while retaining a few rare codons of the original sequence. Since rare codons often have regulatory functions or may be involved in mRNA stability, it may be preferable to retain a few rare codons of the original organism, for example in order to increase the yield of active enzyme. An online tool for harmonization of sequences is, for example, available under "http://codonharmonizer.systemsbiology.nl/" (Claassens et al., Improving heterologous membrane protein production in Escherichia coli by combining transcriptional tuning and codon usage algorithms, PLoS One, 2017). The term "original organism" refers here to the organism from which the nucleotide sequence naturally originates. "Host organism" describes the organism into which the nucleotide sequence is introduced and in which it is expressed recombinantly.

On the basis of known DNA and/or amino acid sequences, it is possible for a person skilled in the art to produce the corresponding nucleic acids right up to complete genes via methods that are generally known nowadays, such as, for example, chemical synthesis or the polymerase chain reaction (PCR) in conjunction with standard methods in molecular biology and/or protein chemistry. Such methods are, for example, known from Sambrook, J., Fritsch, E. F. and Maniatis, T. 2001. Molecular cloning: a laboratory manual, 3rd Edition Cold Spring Laboratory Press.

Furthermore, it is possible to increase the activity of an enzyme in the host organism. For example, to this end, the copy number of the corresponding gene can be increased or the promoter and regulation region or the ribosome binding site that is situated upstream of the structural gene can be mutated. Expression cassettes which are incorporated upstream of the structural gene act in the same way. By means of inducible promoters, it is additionally possible to increase expression at any desired time point. Furthermore, enhancers can, however, also be assigned to the enzyme gene as regulatory sequences, which, via an improved interaction between RNA polymerase and DNA, likewise bring about an increased gene expression. Measures to extend the life span of mRNA likewise improve expression. Furthermore, preventing the degradation of the enzyme protein likewise increases enzyme activity. The genes or gene constructs can either be present in vectors or plasmids with differing copy number or be integrated and amplified in the chromosome. Alternatively, overexpression of the genes in question can also be achieved by altering the media composition and culture control. Instructions in relation to this are found by a person skilled in the art in, inter alia, Martin et al. (Bio/Technology 5, 137-146 (1987)), Guerrero et al. (Gene 138, 35-41 (1994)), Tsuchiya and Morinaga (Bio/Technology 6, 428-430 (1988)), Eikmanns et al. (Gene 102, 93-98 (1991)), EP-A-0 472 869, U.S. Pat. No. 4,601, 893, Schwarzer and Puhler (Bio/Technology 9, 84-87 (1991)), Reinscheid et al. (Applied and Environmental Microbiology 60, 126-132 (1994)), LaBarre et al. (Journal of Bacteriology 175, 1001-1007 (1993)), WO-A-96/15246, Malumbres et al. (Gene 134, 15-24 (1993)), JP-A-10-229891 and Jensen and Hammer (Biotechnology and Bioengineering 58, 191-195 (1998)). Just like the mutations, the measures described above lead to genetically modified cells of the host organism.

Any suitable recombinant method for further development and modification of host enzymes, heterologous enzymes or the host organism in general, which method is known to a person skilled in the art, is preferably usable.

In one embodiment, the first heterologous nucleotide sequence which encodes the prenyltransferase is present in codon-harmonized form. The nucleotide sequence is preferably codon-harmonized for expression in *Saccharomyces cerevisiae* or *Pichia pastoris*, especially for expression in *Saccharomyces cerevisiae*.

In a preferred embodiment, the modified prenyltransferase is based on the prenyltransferase from the *Streptomyces* sp. strain CL190 having the amino acid sequence according to SEQ ID NO: 2, but is modified with respect to said sequence in such a way that at least one amino acid position is changed by substitution, deletion or insertion, preferably by substitution, with respect to the starting enzyme.

The following convention is used herein to describe substitutions affecting exactly one amino acid position (amino acid exchange): the naturally occurring amino acid is designated first in the form of the internationally customary single-letter code, and then followed by the associated sequence position and lastly the inserted amino acid. Multiple exchanges within the same polypeptide chain are separated from one another by slashes. In the case of insertions, additional amino acids are named after the sequence position. In the case of deletions, the missing amino acid is replaced by a symbol, for example an asterisk or a dash, or a Δ is given in front of the corresponding position. For example, Q295F describes the substitution of glutamine at position 295 by phenylalanine. This nomenclature is known to a person skilled in the field of enzyme technology.

The amino acid sequence of the modified prenyltransferase preferably has, based on the numbering according to SEQ ID NO: 2 and with respect to the amino acid sequence of SEQ ID NO: 2, a substitution at at least one of positions 126, 161, 162, 175, 213 or 295; particularly preferably, the amino acid sequence has a substitution at position 295. In various embodiments, 1, 2, 3, 4, 5 or all 6 of the stated positions can be substituted.

The following amino acid residues are present at the stated positions in the wild-type molecule according to SEQ ID NO: 2 of the prenyltransferase from *Streptomyces* sp. strain CL190: T126, Q161, M162, Y175, F213, Q295.

Here, the amino acid positions are defined by an alignment of the amino acid sequence of a prenyltransferase with the amino acid sequence of the prenyltransferase from *Streptomyces* sp. strain CL190 as specified in SEQ ID NO: 2. This assignment is especially also to be used if the amino acid sequence of a prenyltransferase comprises a higher number of amino acid residues than the prenyltransferase from *Streptomyces* sp. strain CL190 according to SEQ ID NO: 2. Proceeding from the stated positions in the amino acid sequence of the prenyltransferase from *Streptomyces* sp. strain CL190, the positions of change in a prenyltransferase are those precisely assigned to said positions in an alignment.

In various embodiments, the amino acid sequence is modified with respect to SEQ ID NO: 2 in such a way that it has at least one of the substitutions 295D, 295F, 295L, 295H, 295N, 295V, 126V, 126G, 161A, 161N, 162A, 175N or 213A. In one embodiment, the amino acid sequence is modified with respect to SEQ ID NO: 2 in such a way that at least the substitutions 126V/161A are present. The amino acid sequence is particularly preferably modified with respect to SEQ ID NO: 2 in such a way that at least one of the substitutions 295F, 295L or 295H is present.

In various embodiments, the amino acid sequence is modified with respect to SEQ ID NO: 2 in such a way that it has at least one of the substitutions Q295D, Q295F, Q295L, Q295H, Q295N, Q295V, T126V, T126G, Q161A, Q161N, M162A, Y175N or F213A. In one embodiment, the amino acid sequence is modified with respect to SEQ ID NO: 2 in such a way that at least the substitutions T126V/Q161A are present. The amino acid sequence is particularly preferably modified with respect to SEQ ID NO: 2 in such a way that at least one of the substitutions Q295F, Q295L or Q295H is present.

In addition to the abovementioned at least one substitution at one of positions 126, 161, 162, 175, 213 and 295, the modified prenyltransferase can have further amino acid substitutions with respect to the starting amino acid sequence according to SEQ ID NO: 2. In such embodiments, the modified prenyltransferase has an amino acid sequence which has at least 80%, further preferably at least 81%, 82%, 83%, 84%, 85%, 86%, 87%, 88%, 89%, 90%, 91%, 92%, 93%, 94%, 95%, 95.5%, 96.0%, 96.5%, 97.0%, 97.2%, 97.4%, 97.6%, 97.8%, 98.0%, 98.2%, 98.4%, 98.6%, 98.8%, 99.0%, 99.1%, 99.2%, 99.3%, 99.4%, 99.5% or 99.6%, sequence identity with the amino acid sequence specified in SEQ ID NO: 2 over the entire length thereof. In one embodiment, the modified prenyltransferase has an amino acid sequence which has at least 99.5% and especially at least 99.6% sequence identity with the amino acid sequence specified in SEQ ID NO: 2 over the entire length thereof. In various embodiments, the amino acid sequence of the modified prenyltransferase corresponds to the sequence specified in SEQ ID NO: 2 with the exception of the at least one substitution at the positions specified above.

In preferred embodiments, the modified prenyltransferase is therefore an enzyme which has an amino acid sequence which has a sequence identity of at least 80%, further preferably of at least 81%, 82%, 83%, 84%, 85%, 86%, 87%, 88%, 89%, 90%, 91%, 92%, 93%, 94%, 95%, 95.5%, 96.0%, 96.5%, 97.0%, 97.2%, 97.4%, 97.6%, 97.8%, 98.0%, 98.2%, 98.4%, 98.6%, 98.8%, 99.0%, 99.1%, 99.2%, 99.3%, 99.4%, 99.5% or 99.6%, with the amino acid sequence specified in SEQ ID NO: 2 over the entire length thereof and has at least one amino acid substitution at at least one of the positions corresponding to positions 126, 161, 162, 175, 213 and 295 in SEQ ID NO: 2, preferably selected from Q295F, Q295L, Q295H, Q295N, Q295D, Q295V, T126V, T126G, Q161A, Q161N, M162A, Y175N and F213A, particularly preferably Q295F, Q295L, or Q295H.

In a preferred embodiment, the modified prenyltransferase has the amino acid sequence specified in SEQ ID NO: 17. The amino acid sequence according to SEQ ID NO: 17 has the amino acid substitution Q295H with respect to the amino acid sequence according to SEQ ID NO: 2. The prenyltransferase according to SEQ ID NO: 17 is, for example, encoded by the nucleotide sequence according to SEQ ID NO: 16 that is codon-harmonized for *Saccharomyces cerevisiae*.

In a further preferred embodiment, the modified prenyltransferase has the amino acid sequence specified in SEQ ID NO: 19. The amino acid sequence according to SEQ ID NO: 19 has the amino acid substitution Q295L with respect to the amino acid sequence according to SEQ ID NO: 2. The prenyltransferase according to SEQ ID NO: 19 is, for example, encoded by the nucleotide sequence according to SEQ ID NO: 18 that is codon-harmonized for *Saccharomyces cerevisiae*.

In particularly preferred embodiments, the modified prenyltransferase has the amino acid sequence specified in SEQ ID NO: 4. The amino acid sequence according to SEQ ID NO: 4 has the amino acid substitution Q295F with respect to the amino acid sequence according to SEQ ID NO: 2. The prenyltransferase according to SEQ ID NO: 4 is, for example, encoded by the nucleotide sequence according to SEQ ID NO: 3 that is codon-harmonized for *Saccharomyces cerevisiae*.

The non-limiting embodiments relate to the use of the above-described prenyltransferases in the methods and also relate to the enzymes as such.

In various embodiments, the prenyltransferase is encoded by a nucleotide sequence which is codon-harmonized for use in the desired host organism.

The nucleic acid molecule which comprises a first heterologous nucleotide sequence which encodes a modified prenyltransferase is preferably introduced into the host organism in the form of a vector or plasmid, for example by transformation, transduction, conjugation or a combination of these methods, preferably by means of transformation. Methods for transforming cells are established in the prior art and are well-known to a person skilled in the art. Heterologous expression is achieved especially by integration of the gene or the alleles into the chromosome of the host organism or with an extrachromosomally replicating vector.

Vectors are understood to mean elements consisting of nucleic acids, which elements contain a nucleic acid as the characterizing nucleic acid region. They are able to establish it as a stable genetic element in a species or a cell line over multiple generations or cell divisions. Vectors are specific plasmids, i.e., circular genetic elements, used especially in bacteria or yeasts. In the context, a nucleic acid is cloned into a vector or can be such a vector. The vectors include, for example, those which originate from bacterial plasmids, viruses or bacteriophages, or predominantly synthetic vectors or plasmids containing elements of greatly differing origin. With the further genetic elements respectively present, vectors are able to establish themselves as stable units in the host cells in question over multiple generations. They can be present extrachromosomally as units of their own or integrate into a chromosome or chromosomal DNA.

Expression vectors comprise nucleotide sequences which enable them to replicate in the host cells containing them, preferably in microorganisms, particularly preferably in unicellular fungi, bacteria or yeasts, and to express a comprised nucleotide sequence there. Expression is influenced especially by the promoter(s) which regulate transcription. In principle, expression can be effected through the natural promoter originally located in front of the nucleic acid to be expressed, but also through a host cell promoter provided on the expression vector or else through a modified or a completely different promoter from another organism or another host cell. In the present case, at least one promoter is provided for the expression of a nucleic acid and used for the expression thereof. Expression vectors can also be regulatable, for example by changing of the culturing conditions or upon attainment of a certain cell density by the host cells containing them or by addition of certain substances, especially activators of gene expression. An example of such a substance is the galactose derivative isopropyl β-D-thiogalactopyranoside (IPTG), which is used as an activator of the bacterial lactose operon (lac operon). Another example is methanol, which acts in *Pichia pastoris* as an activator of the AOX1 gene, which encodes alcohol oxidase I. Furthermore, galactose can be used to regulate the Gal1 and Gal10 promoter in *Saccharomyces cerevisiae*. In contrast to expression vectors, the coding nucleotide sequence present is not expressed in cloning vectors.

Possible as plasmids or vectors are, in principle, all embodiments available to a person skilled in the art for this purpose. Such plasmids and vectors can, for example, be found in the brochures from Novagen, Promega, New England Biolabs, Clontech or Gibco BRL. Further preferred plasmids and vectors can be found in: Glover, D. M. (1985), DNA cloning: a practical approach, Vol. I-III, IRL Press Ltd., Oxford; Rodriguez, R. L. and Denhardt, D. T. (eds) (1988), Vectors: a survey of molecular cloning vectors and their uses, 179-204, Butterworth, Stoneham; Goeddel, D. V. (1990), Systems for heterologous gene expression, Methods Enzymol. 185, 3-7; Sambrook, J., Fritsch, E. F. and Maniatis, T. (1989), Molecular cloning: a laboratory manual, 2nd ed., Cold Spring Harbor Laboratory Press, New York. Suitable vectors are preferably those which are replicated in yeast cells. In a preferred embodiment, the vectors pESC (Agilent Technologies), pGAPZ A and/or pYES2 (Invitrogen, Darmstadt, Germany) or a modified form thereof can be used.

According to a preferred embodiment, the nucleic acid comprises or consists of a nucleotide sequence which encodes an above-described amino acid sequence and is, proceeding from the nucleotide sequence according to SEQ ID NO: 1, modified in such a way that (1) the above-described modified prenyltransferase is encoded and (2) it is optionally additionally adapted to the host organism by being codon-harmonized or codon-optimized.

What may occur is that some of the enzymes and precursors that are required for cannabinoid biosynthesis or the synthesis of cannabigerolic acid are missing in the host organism used, especially in the yeasts *Saccharomyces cerevisiae* or *Pichia pastoris*. The missing enzymes or synthesis pathways can be introduced into the host organism in addition to the modified prenyltransferase in order to form required precursors or substrates or to allow subsequent reactions. Furthermore, enzymes in the host organism can be exchanged or modified in order to increase their activity or stability. Ways of increasing enzyme activity have already been described further above. The host organism naturally produces, for example, only low amounts of geranyl diphosphate. Therefore, an optimization of the mevalonate-dependent isoprenoid biosynthesis pathway is preferred, or the use of host organisms in which it is optimized is preferred.

In a preferred embodiment, the host organism further contains at least one further heterologous nucleic acid molecule which comprises a nucleotide sequence which
(1) encodes a hexanoyl-CoA synthase; and/or
(2) encodes an olivetol synthase and/or
(3) encodes an olivetolic acid cyclase, the host organism containing preferably at least 2, further preferably all 3 sequences.

In a preferred embodiment, the host organism therefore further comprises at least one further heterologous nucleotide sequence, which can likewise be located on the first nucleic acid molecule or on a separate nucleic acid molecule, which (1) encodes a hexanoyl-CoA synthase; and/or
(2) encodes an olivetol synthase and/or
(3) encodes an olivetolic acid cyclase, the host organism containing preferably at least 2, further preferably all 3 sequences.

The hexanoyl-CoA synthase preferentially catalyzes the synthesis of hexanoic acid and coenzyme A to form hexanoyl-coenzyme A. This product forms the precursor for cannabinoid biosynthesis. The nucleic acid sequence which encodes the hexanoyl-CoA synthase preferably originates from *Cannabis sativa* L. However, the nucleic acid sequence can also originate from other organisms known to a person skilled in the art. The associated amino acid sequence of the hexanoyl-CoA synthase preferably comprises or consists of the sequence according to SEQ ID NO: 5. As already described above, variants of said sequence may have at least 80%, further preferably at least 81%, 82%, 83%, 84%, 85%, 86%, 87%, 88%, 89%, 90%, 91%, 92%, 93%, 94%, 95%, 95.5%, 96.0%, 96.5%, 97.0%, 97.2%, 97.4%, 97.6%, 97.8%, 98.0%, 98.2%, 98.4%, 98.6%, 98.8%, 99.0%, 99.1%, 99.2%, 99.3%, 99.4%, 99.5%, 99.6% or 99.7%, sequence identity with the amino acid sequence specified in SEQ ID NO: 5 over the entire length thereof, but with the enzymatic function preferably being maintained in such a way that the variant has at least 80% of the enzyme activity of the enzyme having SEQ ID NO: 5 in a suitable assay. Alternatively, acyl-coenzyme A synthetases, for example ACSM1 from *Bos taurus*, medium-chain fatty acid-CoA ligases, for example FadK from *Escherichia coli*, and/or other enzymes having a corresponding function, for example Faa2p from *Saccharomyces cerevisiae*, can also be used. In an alternative embodiment, enzymes having amino acid sequences according to SEQ ID NO: 24 and/or SEQ ID NO: 25 and/or SEQ ID NO: 26 or variants thereof can be used in addition to or as a replacement for the hexanoyl-CoA synthase.

The olivetol synthase (OLS) preferentially catalyzes the first step of cannabinoid biosynthesis from hexanoyl-CoA and 3 molecules of malonyl-CoA to form 1,3,5,7-tetroxydodecanoyl-CoA. The nucleic acid sequence which encodes the olivetol synthase preferably originates from *Cannabis sativa* L. However, the nucleic acid sequence can also originate from other donor organisms known to a person skilled in the art. The associated amino acid sequence of the olivetol synthase preferably comprises or consists of the sequence according to SEQ ID NO: 6. The variants of said sequence may have at least 80%, further preferably at least 81%, 82%, 83%, 84%, 85%, 86%, 87%, 88%, 89%, 90%, 91%, 92%, 93%, 94%, 95%, 95.5%, 96.0%, 96.5%, 97.0%, 97.2%, 97.4%, 97.6%, 97.8%, 98.0%, 98.2%, 98.4%, 98.6%, 98.8%, 99.0%, 99.1%, 99.2%, 99.3%, 99.4%, 99.5%, 99.6% or 99.7%, sequence identity with the amino acid sequence specified in SEQ ID NO: 6 over the entire length thereof, but with the enzymatic function preferably being maintained in such a way that the variant has at least 80% of the enzyme activity of the enzyme having SEQ ID NO: 6 in a suitable assay.

The olivetolic acid cyclase (OAC) preferentially catalyzes the second step of cannabinoid biosynthesis from 1,3,5,7-tetroxydodecanoyl-CoA to form olivetolic acid. The nucleic acid sequence which encodes the olivetolic acid cyclase preferably originates from *Cannabis sativa* L. However, the nucleic acid sequence can also originate from other donor organisms known to a person skilled in the art. The associated amino acid sequence of the olivetolic acid cyclase preferably comprises or consists of the sequence according to SEQ ID NO: 7. The variants of said sequence may have at least 80%, further preferably at least 81%, 82%, 83%, 84%, 85%, 86%, 87%, 88%, 89%, 90%, 91%, 92%, 93%, 94%, 95%, 95.5%, 96.0%, 96.5%, 97.0%, 97.2%, 97.4%, 97.6%, 97.8%, 98.0%, 98.2%, 98.4%, 98.6%, 98.8%, 99.0%, 99.1%, 99.2%, 99.3%, 99.4%, 99.5%, 99.6% or 99.7%, sequence identity with the amino acid sequence specified in SEQ ID NO: 7 over the entire length thereof, but with the enzymatic function preferably being maintained in such a way that the variant has at least 80% of the enzyme activity of the enzyme having SEQ ID NO: 7 in a suitable assay.

The abovementioned starting enzymes can therefore be modified or optimized, preferably in such a way that the variant has more than 100% of the enzyme activity of the starting enzyme in a suitable assay. Ways of modification have already been described further above.

In a preferred embodiment, the recombinant host organism has an optimized hexanoic acid synthesis pathway.

To optimize the hexanoic acid synthesis pathway in *S. cerevisiae*, the fatty acid synthases in *S. cerevisiae* can be present in a modified form: FAS1(I3016A) and FAS2 (G1250S). A detailed description of these enzyme variants is provided in European patent application EP 3 112 458 A1.

In addition, a nucleic acid molecule which comprises a nucleotide sequence which encodes the fatty acid synthase from *Aspergillus parasiticus* can be introduced into the host organism. The associated amino acid sequences preferably comprise or consist of the subunits according to SEQ ID NO: 8 and SEQ ID NO: 9, and also variants thereof which have at least 80%, further preferably at least 81%, 82%, 83%, 84%, 85%, 86%, 87%, 88%, 89%, 90%, 91%, 92%, 93%, 94%, 95%, 95.5%, 96.0%, 96.5%, 97.0%, 97.2%, 97.4%, 97.6%, 97.8%, 98.0%, 98.2%, 98.4%, 98.6%, 98.8%, 99.0%, 99.1%, 99.2%, 99.3%, 99.4%, 99.5%, 99.6% or 99.7%, sequence identity with the amino acid sequence specified in SEQ ID NO: 8 or 9 over the entire length thereof, the enzymatic function being maintained.

Furthermore, the hexanoic acid synthesis pathway can be optimized by introducing an acetyl-CoA acetyltransferase (AtoB) from *Escherichia coli* and/or a β-ketothiolase (BktB) from *Ralstonia eutropha* and/or a 3-hydroxybutyryl-CoA dehydrogenase (Hbd) and/or a crotonase (Crt) from *Clostridium acetobutylicum* and/or a trans-enoyl-CoA reductase (Ter) from *Treponema denticola* and/or an MCT1 from *Saccharomyces cerevisiae* and/or a TES1 from *K. marxianus* into the host organism. In a preferred embodiment, all of the enzymes described in this paragraph are produced in the host organism. The biosynthesis pathway for hexanoic acid production in *Kluyveromyces marxianus* using the specified enzymes is described in the following publication: Cheon et al., A biosynthetic pathway for hexanoic acid production in *Kluyveromyces marxianus*, J. Biotechnol., 2014, 182-183, 30-36.

Furthermore, it is preferred if the genes AQR1, which preferably encodes a protein having the amino acid sequence according to SEQ ID NO: 20 or variants thereof, (Legras et al., Activation of two different resistance mechanisms in *S. cerevisiae* upon exposure to octanoic and decanoic acids, Appl. Environ. Microbiol., 2010, 76, 7526-7535) and/or PDR12, which preferably encodes a protein having the amino acid sequence according to SEQ ID NO: 21 or variants thereof, (Holyoak et al., The *Saccharomyces cerevisiae* weak-acid-inducible ABC transporter Pdr12 transports fluorescein and preservative anions from the cytosol by an energy-dependent mechanism, J. Bacteriol., 1999, 181, 4644-4652) are downregulated or switched off in the genome of the host organism, preferably in *S. cerevisiae* or in *P. pastoris*. Appropriate techniques are known to a person skilled in the art.

In another, alternative embodiment, the host organism is cultured under conditions in which hexanoic acid is added as a substrate.

In another embodiment, the hexanoic acid synthesis pathway or parts thereof can be present in an optimized form in the host organism and the host organism can additionally be cultured under addition of hexanoic acid.

In a further preferred embodiment, geranyl diphosphate can be provided in the host organism via the mevalonate-dependent isoprenoid synthesis pathway or the methylerythritol phosphate pathway. Geranyl diphosphate is preferably provided in the host organism via the mevalonate-dependent isoprenoid synthesis pathway. The mevalonate-dependent isoprenoid synthesis pathway is further preferably present in an optimized form.

In a preferred embodiment, the following enzymes of the mevalonate-dependent isoprenoid synthesis pathway are produced in the host organism:
 aldehyde dehydrogenase (ALD6) and/or acetyl-CoA synthetase (ACS1/ACS2) and/or acetyl-CoA C-acetyltransferase (ERG10) and/or 3-hydroxy-3-methylglutaryl-CoA synthase (ERG13) and/or 3-hydroxy-3-methylglutaryl-CoA reductase (tHMGR; modified by removing the transmembrane domain of amino acids 1-530) and/or mevalonate kinase (ERG12) and/or phosphomevalonate kinase (ERGS) and/or mevalonate diphosphate decarboxylase (ERG19) and/or isopentenyl diphosphate:dimethylallyl diphosphate isomerase (IDI1). The enzymes listed all originate from the host organism *S. cerevisiae*. The enzymes listed in this paragraph are preferably produced together in the host organism.

Preferably, the farnesyl diphosphate synthetase (ERG20) from *S. cerevisiae* can be present in a modified form or farnesyl diphosphate synthesis in the host organism can be altered. The modification can be effected by, for example, exchanging the native promoter for a weak constitutive promoter in order to downregulate the ERG20 gene. Furthermore, an additional copy of an ERG20-F96W-N127W variant can be introduced into the host organism, which would increase the synthesis of geranyl diphosphate (GPP), and/or a further heterologous geranyl diphosphate synthase (AgGPPS), for example from *Abies grandis*, could be introduced into the host organism (Ignea et al., Engineering monoterpene production in yeast using a synthetic dominant negative geranyl diphosphate synthase, ACS Synth. Biol., 2014, 3, 298-306).

In a further preferred embodiment, the mevalonate-dependent isoprenoid synthesis pathway and/or the hexanoic acid biosynthesis are present in an optimized form in the host organism as described above in addition to the nucleotide sequence which encodes the modified NphB from *Streptomyces* sp. strain CL190. In addition, the nucleic acid(s) used can comprise the nucleotide sequences, preferably from *Cannabis sativa* L., which encode the enzymes hexanoyl-CoA synthase and/or olivetol synthase and/or olivetolic acid cyclase. They can likewise be introduced into the host organism and allow the expression of the associated enzymes.

In a further preferred embodiment, the host organism further comprises at least one further heterologous nucleic acid which comprises a nucleotide sequence which encodes a heterologous enzyme which catalyzes the synthesis or a substep of the synthesis of cannabinoids, especially $\Delta^9$-tetrahydrocannabinolic acid ($\Delta^9$-THCA), cannabidiolic acid (CBDA), cannabichromenic acid (CBCA), tetrahydrocannabinol (THC), cannabidiol (CBD), cannabichromene (CBC) or cannabinolic acid (CBNA), from cannabigerolic acid.

The heterologous enzyme which is encoded by the at least one further heterologous nucleic acid which comprises a nucleotide sequence is further preferably a tetrahydrocannabinolic acid synthase, a cannabidiolic acid synthase or a cannabichromenic acid synthase.

The amino acid sequence of the tetrahydrocannabinolic acid synthase preferably comprises or consists of the amino acid sequence according to SEQ ID NO: 10 or variants thereof which have at least 80%, further preferably at least 81%, 82%, 83%, 84%, 85%, 86%, 87%, 88%, 89%, 90%, 91%, 92%, 93%, 94%, 95%, 95.5%, 96.0%, 96.5%, 97.0%, 97.2%, 97.4%, 97.6%, 97.8%, 98.0%, 98.2%, 98.4%, 98.6%, 98.8%, 99.0%, 99.1%, 99.2%, 99.3%, 99.4%, 99.5%, 99.6% or 99.7%, sequence identity with the amino acid sequence specified in SEQ ID NO: 10 over the entire length thereof, the enzymatic function being maintained (at least 80%, preferably at least 100% of the starting enzyme in a suitable assay).

The amino acid sequence of the cannabidiolic acid synthase further preferably comprises or consists of the amino acid sequence according to SEQ ID NO: 11 or variants thereof which have at least 80%, further preferably at least 810%, 82%, 83%, 84%, 85%, 86%, 87%, 88%, 89%, 90%, 91%, 92%, 93%, 94%, 95%, 95.5%, 96.0%, 96.5%, 97.0%, 97.2%, 97.4%, 97.6%, 97.8%, 98.0%, 98.2%, 98.4%, 98.6%, 98.8%, 99.0%, 99.1%, 99.2%, 99.3%, 99.4%, 99.5%, 99.6% or 99.7%, sequence identity with the amino acid sequence specified in SEQ ID NO: 11 over the entire length thereof, the enzymatic function being maintained (at least 80%, preferably at least 100% of the starting enzyme in a suitable assay).

The nucleotide sequence of the cannabichromenic acid synthase further preferably comprises or consists of the nucleotide sequence specified in SEQ ID NO: 12 or homologs thereof. The associated amino acid sequence is specified under SEQ ID NO: 13. Likewise encompassed are variants thereof which have at least 80%, further preferably at least 81%, 82%, 83%, 84%, 85%, 86%, 87%, 88%, 89%, 90%, 91%, 92%, 93%, 94%, 95%, 95.5%, 96.0%, 96.5%, 97.0%, 97.2%, 97.4%, 97.6%, 97.8%, 98.0%, 98.2%, 98.4%, 98.6%, 98.8%, 99.0%, 99.1%, 99.2%, 99.3%, 99.4%, 99.5%, 99.6% or 99.7%, sequence identity with the amino acid sequence specified in SEQ ID NO: 13 over the entire length thereof, the enzymatic function being maintained (at least 80%, preferably at least 100% of the starting enzyme in a suitable assay).

The host organism can be contacted with the culture medium, cultured and fermented in a continuous or discontinuous manner in a batch process or in a fed-batch process or repeated fed-batch process for the purpose of producing cannabigerolic acid. A summary of the known culturing methods can be found in the textbook by Chmiel ("Bioprozesstechnik 1. Einführung in die Bioverfahrenstechnik" [Bioprocess technology 1. Introduction to bioprocess engineering] (Gustav Fischer Verlag, Stuttgart, 1991)) or in the textbook by Storhas ("Bioreaktoren and periphere Einrichtungen" [Bioreactors and peripheral equipment], Vieweg Verlag, Braunschweig/Wiesbaden, 1994). The culture medium to be used must appropriately meet the demands of the host cell strain in question. Descriptions of culture media for various microorganisms are provided in the manual "Manual of Methods for General Bacteriology" published by the American Society for Bacteriology (Washington D.C., USA, 1981). The product, preferably the cannabigerolic acid formed or a modified form thereof, can either be collected from the medium or be obtained by cell harvesting and subsequent cell disruption. A combination of the two methods is possible as well. The product formed is preferably obtained by cell harvesting and subsequent cell disruption.

At least one sugar, preferably fructose, galactose or glucose, serves as the carbon source in the culture media used. In a preferred embodiment, the host organism is cultured under conditions in which glucose is used as the carbon source, further preferably as the only carbon source.

Organic nitrogen-containing compounds such as peptone, yeast extract, meat extract, malt extract, corn steep liquor, soybean meal and urea or inorganic compounds such as ammonium sulfate, ammonium chloride, ammonium phosphate, ammonium carbonate and ammonium nitrate can be used as nitrogen sources. The nitrogen sources can be used individually or as a mixture.

Phosphoric acid, potassium dihydrogen phosphate or dipotassium hydrogen phosphate or the corresponding sodium-containing salts can be used as the phosphorus source.

The culture medium can furthermore contain metal salts, such as, for example, magnesium sulfate or iron sulfate, which are necessary for the growth of cells.

Lastly, further substances, such as, for example, bases, amino acids, vitamins and/or trace elements, can additionally be added to the medium. Moreover, suitable precursors and substrates can be added to the culture medium. The stated starting materials can be added to the culture in the form of a single batch or appropriately fed in during culturing.

Basic compounds such as sodium hydroxide, potassium hydroxide, ammonia or ammonia water or acidic compounds such as hydrochloric acid, phosphoric acid or sulfuric acid can be appropriately used for pH control of the culture. Antifoam agents such as, for example, fatty acid polyglycol esters can be used to control foaming. Appropriate selectively acting substances such as, for example, antibiotics can be added to the medium to maintain the stability of vectors.

Culturing or fermentation is typically effected at a temperature in the range from 15° C. to 45° C. and preferably at 19° C. to 37° C.

A further embodiment of the method further comprises the step of isolating cannabigerolic acid from the host organism.

In one of these embodiments, the cells of the host organism are lysed in order to isolate cannabigerolic acid from the host organism. The lysis can be done mechanically, for example by means of a French press, glass beads or homogenizer, or chemically. The cells used in the fermentation are preferably treated chemically with an organic solvent. The cell debris can then be separated from the extract. This can preferably be done by means of filtration, sedimentation, centrifugation or a combination of the methods. Any other method known to a person skilled in the art can be used here as well. The products can then preferably be purified, preferably by means of preparative, chromatographic processes.

In a preferred embodiment, the recombinant organism (host organism) or the method has, under a culturing time of at least 5 h, preferably under at least 10 h, 15 h, 20 h, 24 h, 30 h, 35 h, 40 h or 48 h, a production output for cannabigerolic acid of at least 10 nmol/(OD*L*h), further preferably of at least 15 nmol/(OD*L*h), yet further preferably of at least 20 nmol/(OD*L*h), especially of 23 nmol/(OD*L*h). The recombinant organism *S. cerevisiae* or *P. pastoris*, especially *S. cerevisiae*, is preferred. The use of glucose as the only carbon source is preferred in this embodiment. The recombinant organism further preferably produces, besides the modified prenyltransferase, additionally at least one of the enzymes hexanoyl-CoA synthase, olivetol synthase and olivetolic acid cyclase, preferably 2 or all 3 of the enzymes. It is also preferred in this embodiment that the MVA pathway and/or the hexanoic acid biosynthesis in the recombinant organism have been optimized.

A further aspect includes a prenyltransferase as described above in the context of the method and the nucleic acid molecules or nucleotide sequences which encode it. In various embodiments, the nucleic acid molecule as used and as claimed herein is (1) DNA; and/or (2) an expression vector; and/or (3) codon-harmonized for expression in a host organism, preferably in *Saccharomyces cerevisiae*, *Kluyveromyces marxianus*, *Yarrowia lipolytica* or *Pichia pastoris*, further preferably *Saccharomyces cerevisiae* or *Pichia pastoris*, especially *Saccharomyces cerevisiae*.

A further aspect includes a recombinant organism comprising at least one prenyltransferase and/or at least one nucleic acid molecule, especially according to an embodiment described herein.

In one embodiment, the recombinant organism is a microbial organism, especially a yeast cell. In a specific embodiment, the recombinant organism is a *S. cerevisiae* cell, a *K. marxianus* cell, a *Y. lipolytica* cell or a *P. pastoris* cell, further preferably a *S. cerevisiae* cell or a *P. pastoris* cell, especially a *S. cerevisiae* cell.

Further embodiments are present in the claims and the examples. Unless otherwise indicated, the listed nucleotide sequences or the corresponding amino acid sequences thereof can be found in the KEGG database, NCBI database, UniProt database or EMBL database.

The following examples serve to illustrate the non-limiting embodiments without restricting it to these specific embodiments.

This application contains the following FIGURES:

FIG. 1: Formation of CBGA in *S. cerevisiae* cells which were cultured in a bioreactor containing glucose as the carbon source. All biosynthetic genes for forming CBGA were integrated into the genome of the yeast strain.

EXAMPLES

Example 1

Olivetolic acid and geranyl diphosphate were reacted to form the products cannabigerolic acid and 2-O-geranyl olivetolic acid using different NphB variants (SEQ ID NO: 2+substitution indicated). Table 1 shows the results with indication of the molar ratio of cannabigerolic acid and 2-O-geranyl olivetolic acid.

| | CBGA | 2OGOA | CBGA in % | 2OGOA in % |
|---|---|---|---|---|
| WT (SEQ ID NO: 2) | 1 | 5 | 100 | 500 |
| Q161A | 2 | 20 | 200 | 2000 |
| Q161N | 2 | 10 | 190 | 1000 |
| T126V | 4 | 10 | 400 | 1000 |
| T126V/Q161A | 2 | 4 | 200 | 400 |
| F213A | 2 | 120 | 240 | 12000 |
| Y175N | 1 | 2 | 70 | 170 |
| Q295L | 15 | 1 | 1500 | 150 |
| M162A | 0 | 14 | 14 | 1400 |
| T126G | 2 | 5 | 170 | 500 |
| Q295F | 20 | 1 | 2000 | 100 |
| Q295N | 3 | 1 | 300 | 100 |
| Q295V | 1 | 0.5 | 100 | 50 |
| Q295H | 20 | 2 | 2000 | 200 |
| Q295D | 1 | 0.5 | 100 | 50 |

For the mutation Q295F, it was possible to measure a distinctly increased formation of cannabigerolic acid in relation to the formation of 2-O-geranyl olivetolic acid. 20 times more cannabigerolic acid than 2-O-geranyl olivetolic acid was formed. For the mutation Q295L, it was possible to measure a 15 times higher cannabigerolic acid synthesis compared to the 2-O-geranyl olivetolic acid synthesis and, for the mutation Q295H, it was possible to measure 10 times more cannabigerolic acid than 2-O-geranyl olivetolic acid. The product ratios indicated are based here on molar product ratios.

The prenyltransferase variants were expressed in *E. coli* because it was possible to achieve higher protein yields here. The associated nucleotide sequences were codon-optimized beforehand for *E. coli*. An example of an NphB gene nucleotide sequence that is codon-optimized for *E. coli* is listed in SEQ ID NO: 14, without being restricted to said sequence. Exemplary codon-optimized nucleotide sequences for *E. coli* that have a base exchange (codon exchange) at position 883-885 and a second stop codon are listed in SEQ ID NO: 22 and 23, without being restricted to said sequences. For the main culture, 330 ml of LB medium and 200 μg/ml ampicillin were inoculated in a 1 liter shake flask at an $OD_{600}$ of 0.2. The culture was incubated at 30° C. and 160 rpm until it reached an $OD_{600}$ between 0.6 and 0.65. The culture was then cooled to room temperature until it reached an $OD_{600}$ of 0.7. The induction was started with 0.1 g/L lactose and incubated at 25° C. and 160 rpm for 16 hours.

100 μl of activity assay contained 5 mM magnesium chloride, 2 mM GPP, 5 mM olivetolic acid and 80 μl of purified enzyme solution (2 mg/ml) in enzyme buffer (50 mM TRIS-HCl (pH 7.5), 5 mM DTT, 10% (v/v) glycerol, 100 mM NaCl). The activity assays were stopped after 10, 20 and 30 minutes by addition of 290 μL of ice-cold acetonitrile and 10 μL of formic acid. After centrifugation, the supernatant was examined for product formation by means of an HPLC diode array detector (DAD).

Example 2

The modified NphB gene was codon-harmonized for expression in *Saccharomyces cerevisiae* and ordered as a synthetic gene (GeneArt, Life Technologies, Regensburg, Germany). An example of a codon-harmonized nucleotide sequence for *S. cerevisiae* is listed in SEQ ID NO: 15, without being restricted thereto. The gene was cloned into the vector pDionysos (Stehle et al., Heterologous expression of a serine carboxypeptidase-like acyltransferase and characterization of the kinetic mechanism, FEBS J, 2001, 275, 775-87) and the resulting construct was introduced into the host organism by means of transformation.

The production of the enzymes in the host organism was carried out with two precultures followed by a main culture. The first preculture was used for inoculation of the second preculture, which was incubated at 30° C. and 200 rpm for 12 h. 100 ml of complex medium (20 g/L yeast extract, 40 g/L peptone, 80 mg/L adenine hemisulfate, 40 g/L fructose, 5 g/L galactose, 100 mM potassium citrate buffer, pH 5.5) were inoculated to an $OD_{600}$ of 0.5 in 1 L baffled flasks and used as the main culture. The cultures were incubated at 20° C. and 200 rpm for 168 hours.

Cell culture volumes which corresponded to an $OD_{600}$ of 125 were harvested by centrifugation (2000×g, 4° C., 10 min). The supernatants were discarded and the cells were resuspended in 500 μl of buffer (50 mM Tris-HCl buffer, pH 7.5, 10% (v/v) glycerol, 100 mM sodium chloride). The cell suspension was transferred to 0.5 ml tubes and filled with 0.4-0.6 mm glass beads. The cells were lysed by vortexing at maximum speed at 4° C. for 30 minutes. The cell lysate was centrifuged and the supernatant used for NphB activity assays (1 mM GPP, 1 mM OA, 5 mM magnesium chloride, 37° C., 1100 rpm, 4 h). The reaction products were separated chromatographically by means of reversed-phase (RP) HPLC. Purification was performed on a Nucleodur C18 HTec 5 μm (250×10 mm) column (Macherey Nagel, Düren, Germany) using an isocratic gradient (4.0 ml/min, 40° C., 35% (v/v) $H_2O$, 65% (v/v) ACN).

Example 3

The production output of *S. cerevisiae* was measured on the basis of cannabigerolic acid (CBGA) proceeding from glucose as the only carbon source. The MVA pathway and the hexanoic acid biosynthesis were present in an optimized form in the host organism (see the description). The hexanoyl-CoA synthase from *Cannabis sativa*, the olivetol synthase from *Cannabis sativa*, the olivetolic acid cyclase from *Cannabis sativa* and the optimized NphB from *Streptomyces* sp. CL190 were additionally produced in the host organism. The genes were all integrated into the host genome. Known methods for integrating the genes into the host organism are found in the following publications: Apel et al., A Cas9-based toolkit to program gene expression in *Saccharomyces cerevisiae*, Nucleic Acids Res., 2017, 45, 496-508, doi:10.1093/nar/gkw1023; Maury et al., EasyCloneMulti: A Set of Vectors for Simultaneous and Multiple Genomic Integrations in *Saccharomyces cerevisiae*, PLoS One 11, 2016, e0150394, doi:10.1371/journal-.pone.0150394. Culturing was carried out in a bioreactor in complex medium (20 g/L yeast extract, 40 g/L peptone, 80 mg/L adenine hemisulfate, 40 g/L glucose, 5 g/L galactose, 100 mM potassium citrate buffer, pH 5.5). After 24 h, a glucose feed was effected at 2 g/h. After 48 h, it was possible to determine a production output of 23 nmol/(OD*L*h) CBGA (see FIG. 1).

Example 4

The gene of the modified prenyltransferase was cloned into the vector pAX_EV (vector pGAPZ A (Invitrogen, Darmstadt, Germany) with the promoter AOX1 from pPINK_HC (Invitrogen, Darmstadt, Germany) and the resulting construct was introduced into the host organism by means of transformation. For this purpose, electrocompetent cells were transformed with 2 to 3 μg of PmeI-linearized DNA of pAX_NphB at 1800 V using an electroporator. The cells were left to grow on YPD agar containing 100 μg/ml zeocin for 2 days and successful integration into the genome was examined by means of colony PCR. *P. pastoris* cells were incubated in BMGY medium at 30° C. and 200 rpm for 24 hours. The cells were then harvested by centrifugation and resuspended in modified BMMY (1% (v/v) methanol, 10 g/L yeast extract, 20 g/L peptones, 5 g/L casamino acids, 13.8 g/L yeast nitrogen base, 100 mM bis-Tris, pH 5.8, 0.4 mg/L biotin) up to an $OD_{600}$ of 20. Lastly, *Pichia* cells were cultured at 15° C. and 200 rpm. Every 24 h, 0.5% (v/v) methanol was added for induction.

The invention claimed is:

1. A method for recombinant production of cannabigerolic acid in a host organism, the method comprising:
introducing into the host organism a nucleic acid molecule which comprises a first heterologous nucleotide sequence which encodes a modified prenyltransferase; wherein the first heterologous nucleotide sequence has a nucleotide sequence as specified in SEQ ID NO: 15, SEQ ID NO: 16, SEQ ID NO: 18, or SEQ ID NO: 3;
culturing the host organism under conditions to express the nucleotide sequence for encoding the modified prenyltransferase; and
culturing the host organism under conditions to produce cannabigerolic acid.

2. The method according to claim 1, wherein the recombinant host organism has an optimized hexanoic acid synthesis pathway by introducing one or more of the following:
a fatty synthase in a modified form selected from FAS1 (I3016A) and/or FAS2(G1250S);
a nucleic acid molecule that encodes a fatty acid synthase from *A. parasiticus* into the host organism;
an acetyl-CoA acetyltransferase (AtoB) from *E. coli* into the host organism;
a β-ketothiolase (BktB) from *Ralstonia eutropha* into the host organism;
a 3-hydroxybutyryl-CoA dehydrogenase (Hbd) into the host organism;
a crotonase (Crt) from *Clostridium acetobutylicum* into the host organism;
a trans-enoyl-CoA reductase (Ter) from *Treponema denticola* into the host organism;
an MCT1 from *Saccharomyces cerevisiae* into the host organism; and
a TES1 from *K. marxianus* into the host organism.

3. The method according to claim 1, wherein the host organism comprises geranyl diphosphate via the mevalonate-dependent isoprenoid synthesis pathway or the methylerythritol phosphate pathway.

4. The method according to claim 1, wherein the host organism further comprises at least one further heterologous nucleotide sequence which encodes a tetrahydrocannabinolic acid synthase, a cannabidiolic acid synthase, or a cannabichromenic acid synthase.

5. The method according to claim 1, further comprising isolating cannabigerolic acid from the host organism.

6. The method according to claim 1, wherein the product ratio of cannabigerolic acid:2-O-geranyl olivetolic acid is at least 5:1.

7. The method according to claim 2, wherein the fatty acid synthase from *A. parasiticus* has an amino acid sequence having at least 95% sequence identity with the amino acid sequence specified in SEQ ID NO: 8 or SEQ ID NO: 9 over the entire length thereof.

8. The method according to claim 1, wherein the host organism is *Saccharomyces cerevisiae, Kluyveromyces marxianus, Yarrowia hpolytica*, or *Pichia pastoris*.

9. The method according to claim 1, wherein the host organism further comprises at least one further heterologous nucleic acid molecule which comprises a nucleotide sequence that encodes for one or more of the following:
a hexanoyl-CoA synthase having at least 95% sequence identity with the amino acid sequence specified in SEQ ID NO:5,
an olivetol synthase having at least 95% sequence identity with the amino acid sequence specified in SEQ ID NO:6, or
an olivetolic acid cyclase having at least 95% sequence identity with the amino acid sequence specified in SEQ ID NO:7.

10. The method according to claim 1, wherein the modified prenyltransferase being modified comprises a substrate specificity extended to olivetolic acid, and wherein the modified prenyltransferase produces cannabigerolic acid in higher amounts than 2-O-geranyl olivetolic acid as compared to the wild-type prenyltransferase corresponding to SEQ ID NO:2.

11. The method according to claim 9, wherein the at least one further heterologous nucleic acid molecule comprises at least two heterologous nucleic acid molecules that encode for two or more of the following:
a hexanoyl-CoA synthase having at least 95% sequence identity with the amino acid sequence specified in SEQ ID NO: 5,
an olivetol synthase having at least 95% sequence identity with the amino acid sequence specified in SEQ ID NO:6, or
an olivetolic acid cyclase having at least 95% sequence identity with the amino acid sequence specified in SEQ ID NO:7.

12. The method according to claim 9, wherein the at least one further heterologous nucleic acid molecule comprises all three heterologous nucleic acid molecules that encode for the following:
- a hexanoyl-CoA synthase having at least 95% sequence identity with the amino acid sequence specified in SEQ ID NO:5,
- an olivetol synthase having at least 95% sequence identity with the amino acid sequence specified in SEQ ID NO:6, and
- an olivetolic acid cyclase having at least 95% sequence identity with the amino acid sequence specified in SEQ ID NO:7.

* * * * *

```
                            SEQUENCE LISTING

<160> NUMBER OF SEQ ID NOS: 26

<210> SEQ ID NO 1
<211> LENGTH: 924
<212> TYPE: DNA
<213> ORGANISM: Streptomyces sp. CL190

<400> SEQUENCE: 1
atgtccgaag ccgctgatgt cgagcgcgtg tacgcggcca tggaggaagc ggctggactg      60
ctgggtgtgg cctgcgcacg cgacaagatc tatccgctgc tgagcacgtt ccaggacacg     120
ctcgtcgagg gcggcagcgt cgtcgtcttc tccatggcga gcgggcgtca ttccacggaa     180
ctggacttca gcatctcggt gccgaccagc cacggcgacc cgtacgccac cgtcgtggaa     240 aagggctgt ccccggcgac cggccacccc gtggacgacc tgctcgcgga cacccagaag      300
caccttccgg tctccatgtt cgccatcgac ggcgaggtca ccggcggctt caagaagacg     360
tacgccttct tccccaccga acatgcccg gcgtcgccg agctgagcgc catcccctcc       420
atgccgccgg ccgtcgccga gaacgcggag ctgttcgccc gctacggtct ggacaaggtc     480
cagatgacgt cgatggacta caagaagcgg caggtcaacc tctacttcag cgagctgagc     540
gcgcagaccc tggaggcgga atccgtcctc gccctggtgc gcgagctggg cctgcacgtg     600
ccgaacgagc tgggcctgaa gttctgcaag cgctccttct cggtctaccc caccctcaac     660
tgggagaccg gcaagatcga ccggctgtgt ttcgccgtca tctccaacga ccccaccctg     720
gtgccgtcct cggacgaggg cgacatcgag aagttccaca actacgcgac caaggcgccg     780
tacgcgtacg tcggcgagaa gcgcacccta gtctatggc tcacgctgtc gcccaaggag     840
gagtactaca agctgggcgc gtactaccac atcaccgatg tccagcgcgg actgctgaag     900
gcgttcgact cgctggagga ctga                                            924

<210> SEQ ID NO 2
<211> LENGTH: 307
<212> TYPE: PRT
<213> ORGANISM: Streptomyces sp. CL190

<400> SEQUENCE: 2

Met Ser Glu Ala Ala Asp Val Glu Arg Val Tyr Ala Ala Met Glu Glu
1               5                   10                  15

Ala Ala Gly Leu Leu Gly Val Ala Cys Ala Arg Asp Lys Ile Tyr Pro
            20                  25                  30

Leu Leu Ser Thr Phe Gln Asp Thr Leu Val Glu Gly Gly Ser Val Val
        35                  40                  45

Val Phe Ser Met Ala Ser Gly Arg His Ser Thr Glu Leu Asp Phe Ser
    50                  55                  60

Ile Ser Val Pro Thr Ser His Gly Asp Pro Tyr Ala Thr Val Val Glu
65                  70                  75                  80

Lys Gly Leu Phe Pro Ala Thr Gly His Pro Val Asp Asp Leu Leu Ala
                85                  90                  95

Asp Thr Gln Lys His Leu Pro Val Ser Met Phe Ala Ile Asp Gly Glu
            100                 105                 110
```

Val Thr Gly Gly Phe Lys Lys Thr Tyr Ala Phe Phe Pro Thr Asp Asn
            115                 120                 125

Met Pro Gly Val Ala Glu Leu Ser Ala Ile Pro Ser Met Pro Pro Ala
    130                 135                 140

Val Ala Glu Asn Ala Glu Leu Phe Ala Arg Tyr Gly Leu Asp Lys Val
145                 150                 155                 160

Gln Met Thr Ser Met Asp Tyr Lys Lys Arg Gln Val Asn Leu Tyr Phe
                165                 170                 175

Ser Glu Leu Ser Ala Gln Thr Leu Glu Ala Glu Ser Val Leu Ala Leu
            180                 185                 190

Val Arg Glu Leu Gly Leu His Val Pro Asn Glu Leu Gly Leu Lys Phe
        195                 200                 205

Cys Lys Arg Ser Phe Ser Val Tyr Pro Thr Leu Asn Trp Glu Thr Gly
    210                 215                 220

Lys Ile Asp Arg Leu Cys Phe Ala Val Ile Ser Asn Asp Pro Thr Leu
225                 230                 235                 240

Val Pro Ser Ser Asp Glu Gly Asp Ile Glu Lys Phe His Asn Tyr Ala
                245                 250                 255

Thr Lys Ala Pro Tyr Ala Tyr Val Gly Glu Lys Arg Thr Leu Val Tyr
            260                 265                 270

Gly Leu Thr Leu Ser Pro Lys Glu Glu Tyr Tyr Lys Leu Gly Ala Tyr
        275                 280                 285

Tyr His Ile Thr Asp Val Gln Arg Gly Leu Leu Lys Ala Phe Asp Ser
    290                 295                 300

Leu Glu Asp
305

<210> SEQ ID NO 3
<211> LENGTH: 924
<212> TYPE: DNA
<213> ORGANISM: Artificial
<220> FEATURE:
<223> OTHER INFORMATION: NphB-Gen, Codon-harmonisiert fur S. cerevisiae,
      Basenaustausch 883-885 (TTT)

<400> SEQUENCE: 3

```
atgtctgaag cggcggacgt tgaaagagtt tatgctgcta tggaagaagc tgcggggttg      60
ttgggggttg cttgtgcgag agataagata tatccattat tgtccacctt ccaagacacc     120
ttggttgaag gtggttctgt tgttgttttt tctatggctt ctgggcggca ctctacggaa     180
ttggattttt ctatttctgt tccaacctcc catggtgatc catatgctac tgttgttgaa     240
aaagggttgt ttccagctac tggtcatcca gttgatgatt tgttggctga tactcaaaaa     300
catctcccgg tatctatgtt cgctattgat ggtgaagtta ctggtggttt caaaaagact     360
tacgctttct tcccaactga taacatgcca ggtgttgctg aattgtctgc tattccatct     420
atgccaccag ctgttgcaga aaatgctgaa ttatttgcta gatacgggtt ggacaaggtt     480
caaatgactt ctatggatta caagaagaga caagtcaact tgtacttctc gaattgtca     540 gctcaaactt ggaagctga atctgttttg ctttggtta gagaattggg tttacacgtt     600
ccaaacgaat taggttttgaa gttctgcaag agatccttct ctgtttaccc aactttgaat     660
tgggaaaccg gtaaaattga tcggttgtgc tttgccgtta tttccaatga tccaactttg     720
gttccatcct ctgatgaagg tgatatcgaa aagtttcata actacgctac taaggctcca     780
tacgcttatg ttggtgaaaa gagaacttta gtttacgggc tcacttttgtc cccaaaagaa     840 gaatattaca agttgggtgc ctactaccat atcactgatg ttttttcgggg gctcttgaag     900
``` gctttttgatt ctttggaaga ttga    924

<210> SEQ ID NO 4
<211> LENGTH: 307
<212> TYPE: PRT
<213> ORGANISM: Artificial
<220> FEATURE:
<223> OTHER INFORMATION: modifizierte Prenyltransferase, NphB-Q295F

<400> SEQUENCE: 4

Met Ser Glu Ala Ala Asp Val Glu Arg Val Tyr Ala Ala Met Glu Glu
1               5                   10                  15

Ala Ala Gly Leu Leu Gly Val Ala Cys Ala Arg Asp Lys Ile Tyr Pro
            20                  25                  30

Leu Leu Ser Thr Phe Gln Asp Thr Leu Val Glu Gly Gly Ser Val Val
        35                  40                  45

Val Phe Ser Met Ala Ser Gly Arg His Ser Thr Glu Leu Asp Phe Ser
    50                  55                  60

Ile Ser Val Pro Thr Ser His Gly Asp Pro Tyr Ala Thr Val Val Glu
65                  70                  75                  80

Lys Gly Leu Phe Pro Ala Thr His Pro Val Asp Asp Leu Leu Ala
                85                  90                  95

Asp Thr Gln Lys His Leu Pro Val Ser Met Phe Ala Ile Asp Gly Glu
            100                 105                 110

Val Thr Gly Gly Phe Lys Lys Thr Tyr Ala Phe Phe Pro Thr Asp Asn
        115                 120                 125

Met Pro Gly Val Ala Glu Leu Ser Ala Ile Pro Ser Met Pro Pro Ala
    130                 135                 140

Val Ala Glu Asn Ala Glu Leu Phe Ala Arg Tyr Gly Leu Asp Lys Val
145                 150                 155                 160

Gln Met Thr Ser Met Asp Tyr Lys Lys Arg Gln Val Asn Leu Tyr Phe
                165                 170                 175

Ser Glu Leu Ser Ala Gln Thr Leu Glu Ala Glu Ser Val Leu Ala Leu
            180                 185                 190

Val Arg Glu Leu Gly Leu His Val Pro Asn Glu Leu Gly Leu Lys Phe
        195                 200                 205

Cys Lys Arg Ser Phe Ser Val Tyr Pro Thr Leu Asn Trp Glu Thr Gly
    210                 215                 220

Lys Ile Asp Arg Leu Cys Phe Ala Val Ile Ser Asn Asp Pro Thr Leu
225                 230                 235                 240

Val Pro Ser Ser Asp Glu Gly Asp Ile Glu Lys Phe His Asn Tyr Ala
                245                 250                 255

Thr Lys Ala Pro Tyr Ala Tyr Val Gly Glu Lys Arg Thr Leu Val Tyr
            260                 265                 270

Gly Leu Thr Leu Ser Pro Lys Glu Glu Tyr Tyr Lys Leu Gly Ala Tyr
        275                 280                 285

Tyr His Ile Thr Asp Val Phe Arg Gly Leu Leu Lys Ala Phe Asp Ser
    290                 295                 300

Leu Glu Asp
305

<210> SEQ ID NO 5
<211> LENGTH: 720
<212> TYPE: PRT
<213> ORGANISM: Cannabis sativa

<400> SEQUENCE: 5

```
Met Gly Lys Asn Tyr Lys Ser Leu Asp Ser Val Ala Ser Asp Phe
1               5                   10                  15

Ile Ala Leu Gly Ile Thr Ser Glu Val Ala Glu Thr Leu His Gly Arg
            20                  25                  30

Leu Ala Glu Ile Val Cys Asn Tyr Gly Ala Ala Thr Pro Gln Thr Trp
        35                  40                  45

Ile Asn Ile Ala Asn His Ile Leu Ser Pro Asp Leu Pro Phe Ser Leu
    50                  55                  60

His Gln Met Leu Phe Tyr Gly Cys Tyr Lys Asp Phe Gly Pro Ala Pro
65                  70                  75                  80

Pro Ala Trp Ile Pro Asp Pro Glu Lys Val Lys Ser Thr Asn Leu Gly
                85                  90                  95

Ala Leu Leu Glu Lys Arg Gly Lys Glu Phe Leu Gly Val Lys Tyr Lys
            100                 105                 110

Asp Pro Ile Ser Ser Phe Ser His Phe Gln Glu Phe Ser Val Arg Asn
        115                 120                 125

Pro Glu Val Tyr Trp Arg Thr Val Leu Met Asp Glu Met Lys Ile Ser
    130                 135                 140

Phe Ser Lys Asp Pro Glu Cys Ile Leu Arg Arg Asp Asp Ile Asn Asn
145                 150                 155                 160

Pro Gly Gly Ser Glu Trp Leu Pro Gly Gly Tyr Leu Asn Ser Ala Lys
                165                 170                 175

Asn Cys Leu Asn Val Asn Ser Asn Lys Lys Leu Asn Asp Thr Met Ile
            180                 185                 190

Val Trp Arg Asp Glu Gly Asn Asp Asp Leu Pro Leu Asn Lys Leu Thr
        195                 200                 205

Leu Asp Gln Leu Arg Lys Arg Val Trp Leu Val Gly Tyr Ala Leu Glu
    210                 215                 220

Glu Met Gly Leu Glu Lys Gly Cys Ala Ile Ala Ile Asp Met Pro Met
225                 230                 235                 240

His Val Asp Ala Val Val Ile Tyr Leu Ala Ile Val Leu Ala Gly Tyr
                245                 250                 255

Val Val Val Ser Ile Ala Asp Ser Phe Ser Ala Pro Glu Ile Ser Thr
            260                 265                 270

Arg Leu Arg Leu Ser Lys Ala Lys Ala Ile Phe Thr Gln Asp His Ile
        275                 280                 285

Ile Arg Gly Lys Lys Arg Ile Pro Leu Tyr Ser Arg Val Val Glu Ala
    290                 295                 300

Lys Ser Pro Met Ala Ile Val Ile Pro Cys Ser Gly Ser Asn Ile Gly
305                 310                 315                 320

Ala Glu Leu Arg Asp Gly Asp Ile Ser Trp Asp Tyr Phe Leu Glu Arg
                325                 330                 335

Ala Lys Glu Phe Lys Asn Cys Glu Phe Thr Ala Arg Glu Gln Pro Val
            340                 345                 350

Asp Ala Tyr Thr Asn Ile Leu Phe Ser Ser Gly Thr Thr Gly Glu Pro
        355                 360                 365

Lys Ala Ile Pro Trp Thr Gln Ala Thr Pro Leu Lys Ala Ala Ala Asp
    370                 375                 380

Gly Trp Ser His Leu Asp Ile Arg Lys Gly Asp Val Ile Val Trp Pro
385                 390                 395                 400

Thr Asn Leu Gly Trp Met Met Gly Pro Trp Leu Val Tyr Ala Ser Leu
                405                 410                 415
```

```
Leu Asn Gly Ala Ser Ile Ala Leu Tyr Asn Gly Ser Pro Leu Val Ser
                420                 425                 430

Gly Phe Ala Lys Phe Val Gln Asp Ala Lys Val Thr Met Leu Gly Val
            435                 440                 445

Val Pro Ser Ile Val Arg Ser Trp Lys Ser Thr Asn Cys Val Ser Gly
450                 455                 460

Tyr Asp Trp Ser Thr Ile Arg Cys Phe Ser Ser Ser Gly Glu Ala Ser
465                 470                 475                 480

Asn Val Asp Glu Tyr Leu Trp Leu Met Gly Arg Ala Asn Tyr Lys Pro
                485                 490                 495

Val Ile Glu Met Cys Gly Gly Thr Glu Ile Gly Gly Ala Phe Ser Ala
                500                 505                 510

Gly Ser Phe Leu Gln Ala Gln Ser Leu Ser Ser Phe Ser Ser Gln Cys
            515                 520                 525

Met Gly Cys Thr Leu Tyr Ile Leu Asp Lys Asn Gly Tyr Pro Met Pro
        530                 535                 540

Lys Asn Lys Pro Gly Ile Gly Glu Leu Ala Leu Gly Pro Val Met Phe
545                 550                 555                 560

Gly Ala Ser Lys Thr Leu Leu Asn Gly Asn His His Asp Val Tyr Phe
                565                 570                 575

Lys Gly Met Pro Thr Leu Asn Gly Glu Val Leu Arg Arg His Gly Asp
            580                 585                 590

Ile Phe Glu Leu Thr Ser Asn Gly Tyr Tyr His Ala His Gly Arg Ala
        595                 600                 605

Asp Asp Thr Met Asn Ile Gly Gly Ile Lys Ile Ser Ser Ile Glu Ile
        610                 615                 620

Glu Arg Val Cys Asn Glu Val Asp Asp Arg Val Phe Glu Thr Thr Ala
625                 630                 635                 640

Ile Gly Val Pro Pro Leu Gly Gly Gly Pro Glu Gln Leu Val Ile Phe
            645                 650                 655

Phe Val Leu Lys Asp Ser Asn Asp Thr Thr Ile Asp Leu Asn Gln Leu
                660                 665                 670

Arg Leu Ser Phe Asn Leu Gly Leu Gln Lys Lys Leu Asn Pro Leu Phe
            675                 680                 685

Lys Val Thr Arg Val Val Pro Leu Ser Ser Leu Pro Arg Thr Ala Thr
        690                 695                 700

Asn Lys Ile Met Arg Arg Val Leu Arg Gln Gln Phe Ser His Phe Glu
705                 710                 715                 720

<210> SEQ ID NO 6
<211> LENGTH: 385
<212> TYPE: PRT
<213> ORGANISM: Cannabis sativa

<400> SEQUENCE: 6

Met Asn His Leu Arg Ala Glu Gly Pro Ala Ser Val Leu Ala Ile Gly
1               5                   10                  15

Thr Ala Asn Pro Glu Asn Ile Leu Leu Gln Asp Glu Phe Pro Asp Tyr
            20                  25                  30

Tyr Phe Arg Val Thr Lys Ser Glu His Met Thr Gln Leu Lys Glu Lys
        35                  40                  45

Phe Arg Lys Ile Cys Asp Lys Ser Met Ile Arg Lys Arg Asn Cys Phe
    50                  55                  60

Leu Asn Glu Glu His Leu Lys Gln Asn Pro Arg Leu Val Glu His Glu
```

65                  70                  75                  80
Met Gln Thr Leu Asp Ala Arg Gln Asp Met Leu Val Glu Val Pro
                        85                  90                  95

Lys Leu Gly Lys Asp Ala Cys Ala Lys Ala Ile Lys Glu Trp Gly Gln
                100                 105                 110

Pro Lys Ser Lys Ile Thr His Leu Ile Phe Thr Ser Ala Ser Thr Thr
            115                 120                 125

Asp Met Pro Gly Ala Asp Tyr His Cys Ala Lys Leu Leu Gly Leu Ser
        130                 135                 140

Pro Ser Val Lys Arg Val Met Met Tyr Gln Leu Gly Cys Tyr Gly Gly
145                 150                 155                 160

Gly Thr Val Leu Arg Ile Ala Lys Asp Ile Ala Glu Asn Asn Lys Gly
                165                 170                 175

Ala Arg Val Leu Ala Val Cys Cys Asp Ile Met Ala Cys Leu Phe Arg
            180                 185                 190

Gly Pro Ser Glu Ser Asp Leu Glu Leu Leu Val Gly Gln Ala Ile Phe
        195                 200                 205

Gly Asp Gly Ala Ala Ala Val Ile Val Gly Ala Glu Pro Asp Glu Ser
    210                 215                 220

Val Gly Glu Arg Pro Ile Phe Glu Leu Val Ser Thr Gly Gln Thr Ile
225                 230                 235                 240

Leu Pro Asn Ser Glu Gly Thr Ile Gly Gly His Ile Arg Glu Ala Gly
                245                 250                 255

Leu Ile Phe Asp Leu His Lys Asp Val Pro Met Leu Ile Ser Asn Asn
            260                 265                 270

Ile Glu Lys Cys Leu Ile Glu Ala Phe Thr Pro Ile Gly Ile Ser Asp
        275                 280                 285

Trp Asn Ser Ile Phe Trp Ile Thr His Pro Gly Gly Lys Ala Ile Leu
    290                 295                 300

Asp Lys Val Glu Glu Lys Leu His Leu Lys Ser Asp Lys Phe Val Asp
305                 310                 315                 320

Ser Arg His Val Leu Ser Glu His Gly Asn Met Ser Ser Ser Thr Val
                325                 330                 335

Leu Phe Val Met Asp Glu Leu Arg Lys Arg Ser Leu Glu Glu Gly Lys
            340                 345                 350

Ser Thr Thr Gly Asp Gly Phe Glu Trp Gly Val Leu Phe Gly Phe Gly
        355                 360                 365

Pro Gly Leu Thr Val Glu Arg Val Val Arg Ser Val Pro Ile Lys
    370                 375                 380

Tyr
385

<210> SEQ ID NO 7
<211> LENGTH: 101
<212> TYPE: PRT
<213> ORGANISM: Cannabis sativa

<400> SEQUENCE: 7

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Val Asn Leu Val Asn
                20                  25                  30

Ile Ile Pro Ala Met Lys Asp Val Tyr Trp Gly Lys Asp Val Thr Gln
            35                  40                  45

```
Lys Asn Lys Glu Glu Gly Tyr Thr His Ile Val Glu Val Thr Phe Glu
    50                  55                  60

Ser Val Glu Thr Ile Gln Asp Tyr Ile Ile His Pro Ala His Val Gly
65                  70                  75                  80

Phe Gly Asp Val Tyr Arg Ser Phe Trp Glu Lys Leu Leu Ile Phe Asp
                    85                  90                  95

Tyr Thr Pro Arg Lys
            100

<210> SEQ ID NO 8
<211> LENGTH: 1671
<212> TYPE: PRT
<213> ORGANISM: Aspergillus parasiticus

<400> SEQUENCE: 8

Met Val Ile Gln Gly Lys Arg Leu Ala Ala Ser Ser Ile Gln Leu Leu
1               5                   10                  15

Ala Ser Ser Leu Asp Ala Lys Lys Leu Cys Tyr Glu Tyr Asp Glu Arg
                20                  25                  30

Gln Ala Pro Gly Val Thr Gln Ile Thr Glu Glu Ala Pro Thr Glu Gln
                35                  40                  45

Pro Pro Leu Ser Thr Pro Pro Ser Leu Pro Gln Thr Pro Asn Ile Ser
50                  55                  60

Pro Ile Ser Ala Ser Lys Ile Val Ile Asp Asp Val Ala Leu Ser Arg
65                  70                  75                  80

Val Gln Ile Val Gln Ala Leu Val Ala Arg Lys Leu Lys Thr Ala Ile
                85                  90                  95

Ala Gln Leu Pro Thr Ser Lys Ser Ile Lys Glu Leu Ser Gly Gly Arg
                100                 105                 110

Ser Ser Leu Gln Asn Glu Leu Val Gly Asp Ile His Asn Glu Phe Ser
                115                 120                 125

Ser Ile Pro Asp Ala Pro Glu Gln Ile Leu Leu Arg Asp Phe Gly Asp
                130                 135                 140

Ala Asn Pro Thr Val Gln Leu Gly Lys Thr Ser Ser Ala Ala Val Ala
145                 150                 155                 160

Lys Leu Ile Ser Ser Lys Met Pro Ser Asp Phe Asn Ala Asn Ala Ile
                165                 170                 175

Arg Ala His Leu Ala Asn Lys Trp Gly Leu Gly Pro Leu Arg Gln Thr
                180                 185                 190

Ala Val Leu Leu Tyr Ala Ile Ala Ser Glu Pro Pro Ser Arg Leu Ala
                195                 200                 205

Ser Ser Ser Ala Ala Glu Glu Tyr Trp Asp Asn Val Ser Ser Met Tyr
                210                 215                 220

Ala Glu Ser Cys Gly Ile Thr Leu Arg Pro Arg Gln Asp Thr Met Asn
225                 230                 235                 240

Glu Asp Ala Met Ala Ser Ser Ile Asp Pro Ala Val Val Ala Glu
                245                 250                 255

Phe Ser Lys Gly His Arg Arg Leu Gly Val Gln Gln Phe Gln Ala Leu
                260                 265                 270

Ala Glu Tyr Leu Gln Ile Asp Leu Ser Gly Ser Gln Ala Ser Gln Ser
                275                 280                 285

Asp Ala Leu Val Ala Glu Leu Gln Gln Lys Val Asp Leu Trp Thr Ala
                290                 295                 300

Glu Met Thr Pro Glu Phe Leu Ala Gly Ile Ser Pro Met Leu Asp Val
305                 310                 315                 320
```

```
Lys Lys Ser Arg Arg Tyr Gly Ser Trp Trp Asn Met Ala Arg Gln Asp
            325                 330                 335

Val Leu Ala Phe Tyr Arg Arg Pro Ser Tyr Ser Glu Phe Val Asp Asp
            340                 345                 350

Ala Leu Ala Phe Lys Val Phe Leu Asn Arg Leu Cys Asn Arg Ala Asp
            355                 360                 365

Glu Ala Leu Leu Asn Met Val Arg Ser Leu Ser Cys Asp Ala Tyr Phe
            370                 375                 380

Lys Gln Gly Ser Leu Pro Gly Tyr His Ala Ala Ser Arg Leu Leu Glu
385                 390                 395                 400

Gln Ala Ile Thr Ser Thr Val Ala Asp Cys Pro Lys Ala Arg Leu Ile
            405                 410                 415

Leu Pro Ala Val Gly Pro His Thr Thr Ile Thr Lys Asp Gly Thr Ile
            420                 425                 430

Glu Tyr Ala Glu Ala Pro Arg Gln Gly Val Ser Gly Pro Thr Ala Tyr
            435                 440                 445

Ile Gln Ser Leu Arg Gln Gly Ala Ser Phe Ile Gly Leu Lys Ser Ala
            450                 455                 460

Asp Val Asp Thr Gln Ser Asn Leu Thr Asp Ala Leu Leu Asp Ala Met
465                 470                 475                 480

Cys Leu Ala Leu His Asn Gly Ile Ser Phe Val Gly Lys Thr Phe Leu
            485                 490                 495

Val Thr Gly Ala Gly Gln Gly Ser Ile Gly Ala Gly Val Val Arg Leu
            500                 505                 510

Leu Leu Glu Gly Gly Ala Arg Val Leu Val Thr Thr Ser Arg Glu Pro
            515                 520                 525

Ala Thr Thr Ser Arg Tyr Phe Gln Gln Met Tyr Asp Asn His Gly Ala
            530                 535                 540

Lys Phe Ser Glu Leu Arg Val Val Pro Cys Asn Leu Ala Ser Ala Gln
545                 550                 555                 560

Asp Cys Glu Gly Leu Ile Arg His Val Tyr Asp Pro Arg Gly Leu Asn
            565                 570                 575

Trp Asp Leu Asp Ala Ile Leu Pro Phe Ala Ala Ala Ser Asp Tyr Ser
            580                 585                 590

Thr Glu Met His Asp Ile Arg Gly Gln Ser Glu Leu Gly His Arg Leu
            595                 600                 605

Met Leu Val Asn Val Phe Arg Val Leu Gly His Ile Val His Cys Lys
            610                 615                 620

Arg Asp Ala Gly Val Asp Cys His Pro Thr Gln Val Leu Leu Pro Leu
625                 630                 635                 640

Ser Pro Asn His Gly Ile Phe Gly Gly Asp Gly Met Tyr Pro Glu Ser
            645                 650                 655

Lys Leu Ala Leu Glu Ser Leu Phe His Arg Ile Arg Ser Glu Ser Trp
            660                 665                 670

Ser Asp Gln Leu Ser Ile Cys Gly Val Arg Ile Gly Trp Thr Arg Ser
            675                 680                 685

Thr Gly Leu Met Thr Ala His Asp Ile Ile Ala Glu Thr Val Glu Glu
            690                 695                 700

His Gly Ile Arg Thr Phe Ser Val Ala Glu Met Ala Leu Asn Ile Ala
705                 710                 715                 720

Met Leu Leu Thr Pro Asp Phe Val Ala His Cys Glu Asp Gly Pro Leu
            725                 730                 735
```

Asp Ala Asp Phe Thr Gly Ser Leu Gly Thr Leu Gly Ser Ile Pro Gly
            740                 745                 750

Phe Leu Ala Gln Leu His Gln Lys Val Gln Leu Ala Ala Glu Val Ile
            755                 760                 765

Arg Ala Val Gln Ala Glu Asp Glu His Glu Arg Phe Leu Ser Pro Gly
            770                 775                 780

Thr Lys Pro Thr Leu Gln Ala Pro Val Ala Pro Met His Pro Arg Ser
785                 790                 795                 800

Ser Leu Arg Val Gly Tyr Pro Arg Leu Pro Asp Tyr Glu Gln Glu Ile
                805                 810                 815

Arg Pro Leu Ser Pro Arg Leu Glu Arg Leu Gln Asp Pro Ala Asn Ala
            820                 825                 830

Val Val Val Val Gly Tyr Ser Glu Leu Gly Pro Trp Gly Ser Ala Arg
            835                 840                 845

Leu Arg Trp Glu Ile Glu Ser Gln Gly Gln Trp Thr Ser Ala Gly Tyr
            850                 855                 860

Val Glu Leu Ala Trp Leu Met Asn Leu Ile Arg His Val Asn Asp Glu
865                 870                 875                 880

Ser Tyr Val Gly Trp Val Asp Thr Gln Thr Gly Lys Pro Val Arg Asp
                885                 890                 895

Gly Glu Ile Gln Ala Leu Tyr Gly Asp His Ile Asp Asn His Thr Gly
            900                 905                 910

Ile Arg Pro Ile Gln Ser Thr Ser Tyr Asn Pro Glu Arg Met Glu Val
            915                 920                 925

Leu Gln Glu Val Ala Val Glu Glu Asp Leu Pro Glu Phe Glu Val Ser
            930                 935                 940

Gln Leu Thr Ala Asp Ala Met Arg Leu Arg His Gly Ala Asn Val Ser
945                 950                 955                 960

Ile Arg Pro Ser Gly Asn Pro Asp Ala Cys His Val Lys Leu Lys Arg
                965                 970                 975

Gly Ala Val Ile Leu Val Pro Lys Thr Val Pro Phe Val Trp Gly Ser
            980                 985                 990

Cys Ala Gly Glu Leu Pro Lys Gly Trp Thr Pro Ala Lys Tyr Gly Ile
            995                 1000                1005

Pro Glu Asn Leu Ile His Gln Val Asp Pro Val Thr Leu Tyr Thr
            1010                1015                1020

Ile Cys Cys Val Ala Glu Ala Phe Tyr Ser Ala Gly Ile Thr His
            1025                1030                1035

Pro Leu Glu Val Phe Arg His Ile His Leu Ser Glu Leu Gly Asn
            1040                1045                1050

Phe Ile Gly Ser Ser Met Gly Gly Pro Thr Lys Thr Arg Gln Leu
            1055                1060                1065

Tyr Arg Asp Val Tyr Phe Asp His Glu Ile Pro Ser Asp Val Leu
            1070                1075                1080

Gln Asp Thr Tyr Leu Asn Thr Pro Ala Ala Trp Val Asn Met Leu
            1085                1090                1095

Leu Leu Gly Cys Thr Gly Pro Ile Lys Thr Pro Val Gly Ala Cys
            1100                1105                1110

Ala Thr Gly Val Glu Ser Ile Asp Ser Gly Tyr Glu Ser Ile Met
            1115                1120                1125

Ala Gly Lys Thr Lys Met Cys Leu Val Gly Gly Tyr Asp Asp Leu
            1130                1135                1140

Gln Glu Glu Ala Ser Tyr Gly Phe Ala Gln Leu Lys Ala Thr Val

```
            1145                1150                1155
Asn Val Glu Glu Glu Ile Ala Cys Gly Arg Gln Pro Ser Glu Met
            1160                1165                1170
Ser Arg Pro Met Ala Glu Ser Arg Ala Gly Phe Val Glu Ala His
            1175                1180                1185
Gly Cys Gly Val Gln Leu Leu Cys Arg Gly Asp Ile Ala Leu Gln
            1190                1195                1200
Met Gly Leu Pro Ile Tyr Ala Val Ile Ala Ser Ser Ala Met Ala
            1205                1210                1215
Ala Asp Lys Ile Gly Ser Ser Val Pro Ala Pro Gly Gln Gly Ile
            1220                1225                1230
Leu Ser Phe Ser Arg Glu Arg Ala Arg Ser Ser Met Ile Ser Val
            1235                1240                1245
Thr Ser Arg Pro Ser Ser Arg Ser Ser Thr Ser Ser Glu Val Ser
            1250                1255                1260
Asp Lys Ser Ser Leu Thr Ser Ile Thr Ser Ile Ser Asn Pro Ala
            1265                1270                1275
Pro Arg Ala Gln Arg Ala Arg Ser Thr Thr Asp Met Ala Pro Leu
            1280                1285                1290
Arg Ala Ala Leu Ala Thr Trp Gly Leu Thr Ile Asp Asp Leu Asp
            1295                1300                1305
Val Ala Ser Leu His Gly Thr Ser Thr Arg Gly Asn Asp Leu Asn
            1310                1315                1320
Glu Pro Glu Val Ile Glu Thr Gln Met Arg His Leu Gly Arg Thr
            1325                1330                1335
Pro Gly Arg Pro Leu Trp Ala Ile Cys Gln Lys Ser Val Thr Gly
            1340                1345                1350
His Pro Lys Ala Pro Ala Ala Ala Trp Met Leu Asn Gly Cys Leu
            1355                1360                1365
Gln Val Leu Asp Ser Gly Leu Val Pro Gly Asn Arg Asn Leu Asp
            1370                1375                1380
Thr Leu Asp Glu Ala Leu Arg Ser Ala Ser His Leu Cys Phe Pro
            1385                1390                1395
Thr Arg Thr Val Gln Leu Arg Glu Val Lys Ala Phe Leu Leu Thr
            1400                1405                1410
Ser Phe Gly Phe Gly Gln Lys Gly Gly Gln Val Val Gly Val Ala
            1415                1420                1425
Pro Lys Tyr Phe Phe Ala Thr Leu Pro Arg Pro Glu Val Glu Gly
            1430                1435                1440
Tyr Tyr Arg Lys Val Arg Val Arg Thr Glu Ala Gly Asp Arg Ala
            1445                1450                1455
Tyr Ala Ala Ala Val Met Ser Gln Ala Val Val Lys Ile Gln Thr
            1460                1465                1470
Gln Asn Pro Tyr Asp Glu Pro Asp Ala Pro Arg Ile Phe Leu Asp
            1475                1480                1485
Pro Leu Ala Arg Ile Ser Gln Asp Pro Ser Thr Gly Gln Tyr Arg
            1490                1495                1500
Phe Arg Ser Asp Ala Thr Pro Ala Leu Asp Asp Ala Leu Pro
            1505                1510                1515
Pro Pro Gly Glu Pro Thr Glu Leu Val Lys Gly Ile Ser Ser Ala
            1520                1525                1530
Trp Ile Glu Glu Lys Val Arg Pro His Met Ser Pro Gly Gly Thr
            1535                1540                1545
```

```
Val Gly Val Asp Leu Val Pro Leu Ala Ser Phe Asp Ala Tyr Lys
    1550             1555                 1560

Asn Ala Ile Phe Val Glu Arg Asn Tyr Thr Val Arg Glu Arg Asp
    1565             1570                 1575

Trp Ala Glu Lys Ser Ala Asp Val Arg Ala Ala Tyr Ala Ser Arg
    1580             1585                 1590

Trp Cys Ala Lys Glu Ala Val Phe Lys Cys Leu Gln Thr His Ser
    1595             1600                 1605

Gln Gly Ala Gly Ala Ala Met Lys Glu Ile Glu Ile Glu His Gly
    1610             1615                 1620

Gly Asn Gly Ala Pro Lys Val Lys Leu Arg Gly Ala Ala Gln Thr
    1625             1630                 1635

Ala Ala Arg Gln Arg Gly Leu Glu Gly Val Gln Leu Ser Ile Ser
    1640             1645                 1650

Tyr Gly Asp Asp Ala Val Ile Ala Val Ala Leu Gly Leu Met Ser
    1655             1660                 1665

Gly Ala Ser
    1670

<210> SEQ ID NO 9
<211> LENGTH: 1888
<212> TYPE: PRT
<213> ORGANISM: Aspergillus parasiticus

<400> SEQUENCE: 9

Met Gly Ser Val Ser Arg Glu His Glu Ser Ile Pro Ile Gln Ala Ala
1               5                   10                  15

Gln Arg Gly Ala Ala Arg Ile Cys Ala Ala Phe Gly Gly Gln Gly Ser
                20                  25                  30

Asn Asn Leu Asp Val Leu Lys Gly Leu Leu Glu Leu Tyr Lys Arg Tyr
            35                  40                  45

Gly Pro Asp Leu Asp Glu Leu Leu Asp Val Ala Ser Asn Thr Leu Ser
        50                  55                  60

Gln Leu Ala Ser Ser Pro Ala Ala Ile Asp Val His Glu Pro Trp Gly
65                  70                  75                  80

Phe Asp Leu Arg Gln Trp Leu Thr Thr Pro Glu Val Ala Pro Ser Lys
                85                  90                  95

Glu Ile Leu Ala Leu Pro Pro Arg Ser Phe Pro Leu Asn Thr Leu Leu
                100                 105                 110

Ser Leu Ala Leu Tyr Cys Ala Thr Cys Arg Glu Leu Glu Leu Asp Pro
            115                 120                 125

Gly Gln Phe Arg Ser Leu Leu His Ser Ser Thr Gly His Ser Gln Gly
        130                 135                 140

Ile Leu Ala Ala Val Ala Ile Thr Gln Ala Glu Ser Trp Pro Thr Phe
145                 150                 155                 160

Tyr Asp Ala Cys Arg Thr Val Leu Gln Ile Ser Phe Trp Ile Gly Leu
                165                 170                 175

Glu Ala Tyr Leu Phe Thr Pro Ser Ser Ala Ala Ser Asp Ala Met Ile
                180                 185                 190

Gln Asp Cys Ile Glu His Gly Glu Gly Leu Leu Ser Ser Met Leu Ser
            195                 200                 205

Val Ser Gly Leu Ser Arg Ser Gln Val Glu Arg Val Ile Glu His Val
        210                 215                 220

Asn Lys Gly Leu Gly Glu Cys Asn Arg Trp Val His Leu Ala Leu Val
```

```
            225                 230                 235                 240
        Asn Ser His Glu Lys Phe Val Leu Ala Gly Pro Pro Gln Ser Leu Trp
                            245                 250                 255

Ala Val Cys Leu His Val Arg Arg Ile Arg Ala Asp Asn Asp Leu Asp
                        260                 265                 270

Gln Ser Arg Ile Leu Phe Arg Asn Arg Lys Pro Ile Val Asp Ile Leu
                    275                 280                 285

Phe Leu Pro Ile Ser Ala Pro Phe His Thr Pro Tyr Leu Asp Gly Val
                290                 295                 300

Gln Asp Arg Val Ile Glu Ala Leu Ser Ser Ala Ser Leu Ala Leu His
        305                 310                 315                 320

Ser Ile Lys Ile Pro Leu Tyr His Thr Gly Thr Gly Ser Asn Leu Gln
                            325                 330                 335

Glu Leu Gln Pro His Gln Leu Ile Pro Thr Leu Ile Arg Ala Ile Thr
                        340                 345                 350

Val Asp Gln Leu Asp Trp Pro Leu Val Cys Arg Gly Leu Asn Ala Thr
                    355                 360                 365

His Val Leu Asp Phe Gly Pro Gly Gln Thr Cys Ser Leu Ile Gln Glu
                370                 375                 380

Leu Thr Gln Gly Thr Gly Val Ser Val Ile Gln Leu Thr Thr Gln Ser
        385                 390                 395                 400

Gly Pro Lys Pro Val Gly Gly His Leu Ala Ala Val Asn Trp Glu Ala
                            405                 410                 415

Glu Phe Gly Leu Arg Leu His Ala Asn Val His Gly Ala Ala Lys Leu
                        420                 425                 430

His Asn Arg Met Thr Thr Leu Leu Gly Lys Pro Pro Val Met Val Ala
                    435                 440                 445

Gly Met Thr Pro Thr Thr Val Arg Trp Asp Phe Val Ala Ala Val Ala
                450                 455                 460

Gln Ala Gly Tyr His Val Glu Leu Ala Gly Gly Tyr His Ala Glu
        465                 470                 475                 480

Arg Gln Phe Glu Ala Glu Ile Arg Arg Leu Thr Ala Ile Pro Ala
                            485                 490                 495

Asp His Gly Ile Thr Cys Asn Leu Leu Tyr Ala Lys Pro Thr Thr Phe
                        500                 505                 510

Ser Trp Gln Ile Ser Val Ile Lys Asp Leu Val Arg Gln Gly Val Pro
                    515                 520                 525

Val Glu Gly Ile Thr Ile Gly Ala Gly Ile Pro Ser Pro Glu Val Val
                530                 535                 540

Gln Glu Cys Val Gln Ser Ile Gly Leu Lys His Ile Ser Phe Lys Pro
        545                 550                 555                 560

Gly Ser Phe Glu Ala Ile His Gln Val Ile Gln Ile Ala Arg Thr His
                            565                 570                 575

Pro Asn Phe Leu Ile Gly Leu Gln Trp Thr Ala Gly Arg Gly Gly Gly
                        580                 585                 590

His His Ser Trp Glu Asp Phe His Gly Pro Ile Leu Ala Thr Tyr Ala
                    595                 600                 605

Gln Ile Arg Ser Cys Pro Asn Ile Leu Leu Val Val Gly Ser Gly Phe
                610                 615                 620

Gly Gly Gly Pro Asp Thr Phe Pro Tyr Leu Thr Gly Gln Trp Ala Gln
        625                 630                 635                 640

Ala Phe Gly Tyr Pro Cys Met Pro Phe Asp Gly Val Leu Leu Gly Ser
                            645                 650                 655
```

-continued

Arg Met Met Val Ala Arg Glu Ala His Thr Ser Ala Gln Ala Lys Arg
         660                 665                 670

Leu Ile Ile Asp Ala Gln Gly Val Gly Asp Ala Asp Trp His Lys Ser
         675                 680                 685

Phe Asp Glu Pro Thr Gly Gly Val Val Thr Val Asn Ser Glu Phe Gly
690                  695                 700

Gln Pro Ile His Val Leu Ala Thr Arg Gly Val Met Leu Trp Lys Glu
705                  710                 715                 720

Leu Asp Asn Arg Val Phe Ser Ile Lys Asp Thr Ser Lys Arg Leu Glu
             725                 730                 735

Tyr Leu Arg Asn His Arg Gln Glu Ile Val Ser Arg Leu Asn Ala Asp
             740                 745                 750

Phe Ala Arg Pro Trp Phe Ala Val Asp Gly His Gly Gln Asn Val Glu
         755                 760                 765

Leu Glu Asp Met Thr Tyr Leu Glu Val Leu Arg Arg Leu Cys Asp Leu
         770                 775                 780

Thr Tyr Val Ser His Gln Lys Arg Trp Val Asp Pro Ser Tyr Arg Ile
785                  790                 795                 800

Leu Leu Leu Asp Phe Val His Leu Leu Arg Glu Arg Phe Gln Cys Ala
                 805                 810                 815

Ile Asp Asn Pro Gly Glu Tyr Pro Leu Asp Ile Ile Val Arg Val Glu
             820                 825                 830

Glu Ser Leu Lys Asp Lys Ala Tyr Arg Thr Leu Tyr Pro Glu Asp Val
         835                 840                 845

Ser Leu Leu Met His Leu Phe Ser Arg Arg Asp Ile Lys Pro Val Pro
850                  855                 860

Phe Ile Pro Arg Leu Asp Glu Arg Phe Glu Thr Trp Phe Lys Lys Asp
865                  870                 875                 880

Ser Leu Trp Gln Ser Glu Asp Val Glu Ala Val Ile Gly Gln Asp Val
                 885                 890                 895

Gln Arg Ile Phe Ile Ile Gln Gly Pro Met Ala Val Gln Tyr Ser Ile
             900                 905                 910

Ser Asp Asp Glu Ser Val Lys Asp Ile Leu His Asn Ile Cys Asn His
         915                 920                 925

Tyr Val Glu Ala Leu Gln Ala Asp Ser Arg Gly Thr Ser Ile Gly Asp
         930                 935                 940

Val His Ser Ile Thr Gln Lys Pro Leu Ser Ala Phe Pro Gly Leu Lys
945                  950                 955                 960

Val Thr Thr Asn Arg Val Gln Gly Leu Tyr Lys Phe Glu Lys Val Gly
             965                 970                 975

Ala Val Pro Glu Met Asp Val Leu Phe Glu His Ile Val Gly Leu Ser
         980                 985                 990

Lys Ser Trp Ala Arg Thr Cys Leu Met Ser Lys Ser Val Phe Arg Asp
         995                 1000                1005

Gly Ser Arg Leu His Asn Pro Ile Arg Ala Ala Leu Gln Leu Gln
         1010            1015            1020

Arg Gly Asp Thr Ile Glu Val Leu Leu Thr Ala Asp Ser Glu Ile
         1025            1030            1035

Arg Lys Ile Arg Leu Ile Ser Pro Thr Gly Asp Gly Gly Ser Thr
         1040            1045            1050

Ser Lys Val Val Leu Glu Ile Val Ser Asn Asp Gly Gln Arg Val
         1055            1060            1065

```
Phe Ala Thr Leu Ala Pro Asn Ile Pro Leu Ser Pro Glu Pro Ser
    1070            1075            1080

Val Val Phe Cys Phe Lys Val Asp Gln Lys Pro Asn Glu Trp Thr
    1085            1090            1095

Leu Glu Glu Asp Ala Ser Gly Arg Ala Glu Arg Ile Lys Ala Leu
    1100            1105            1110

Tyr Met Ser Leu Trp Asn Leu Gly Phe Pro Asn Lys Ala Ser Val
    1115            1120            1125

Leu Gly Leu Asn Ser Gln Phe Thr Gly Glu Glu Leu Met Ile Thr
    1130            1135            1140

Thr Asp Lys Ile Arg Asp Phe Glu Arg Val Leu Arg Gln Thr Ser
    1145            1150            1155

Pro Leu Gln Leu Gln Ser Trp Asn Pro Gln Gly Cys Val Pro Ile
    1160            1165            1170

Asp Tyr Cys Val Val Ile Ala Trp Ser Ala Leu Thr Lys Pro Leu
    1175            1180            1185

Met Val Ser Ser Leu Lys Cys Asp Leu Leu Asp Leu Leu His Ser
    1190            1195            1200

Ala Ile Ser Phe His Tyr Ala Pro Ser Val Lys Pro Leu Arg Val
    1205            1210            1215

Gly Asp Ile Val Lys Thr Ser Ser Arg Ile Leu Ala Val Ser Val
    1220            1225            1230

Arg Pro Arg Gly Thr Met Leu Thr Val Ser Ala Asp Ile Gln Arg
    1235            1240            1245

Gln Gly Gln His Val Val Thr Val Lys Ser Asp Phe Phe Leu Gly
    1250            1255            1260

Gly Pro Val Leu Ala Cys Glu Thr Pro Phe Glu Leu Thr Glu Glu
    1265            1270            1275

Pro Glu Met Val Val His Val Asp Ser Glu Val Arg Arg Ala Ile
    1280            1285            1290

Leu His Ser Arg Lys Trp Leu Met Arg Glu Asp Arg Ala Leu Asp
    1295            1300            1305

Leu Leu Gly Arg Gln Leu Leu Phe Arg Leu Lys Ser Glu Lys Leu
    1310            1315            1320

Phe Arg Pro Asp Gly Gln Leu Ala Leu Leu Gln Val Thr Gly Ser
    1325            1330            1335

Val Phe Ser Tyr Ser Pro Asp Gly Ser Thr Thr Ala Phe Gly Arg
    1340            1345            1350

Val Tyr Phe Glu Ser Glu Ser Cys Thr Gly Asn Val Val Met Asp
    1355            1360            1365

Phe Leu His Arg Tyr Gly Ala Pro Arg Ala Gln Leu Leu Glu Leu
    1370            1375            1380

Gln His Pro Gly Trp Thr Gly Thr Ser Thr Val Ala Val Arg Gly
    1385            1390            1395

Pro Arg Arg Ser Gln Ser Tyr Ala Arg Val Ser Leu Asp His Asn
    1400            1405            1410

Pro Ile His Val Cys Pro Ala Phe Ala Arg Tyr Ala Gly Leu Ser
    1415            1420            1425

Gly Pro Ile Val His Gly Met Glu Thr Ser Ala Met Met Arg Arg
    1430            1435            1440

Ile Ala Glu Trp Ala Ile Gly Asp Ala Asp Arg Ser Arg Phe Arg
    1445            1450            1455

Ser Trp His Ile Thr Leu Gln Ala Pro Val His Pro Asn Asp Pro
```

```
                1460                1465                1470
Leu Arg Val Glu Leu Gln His Lys Ala Met Glu Asp Gly Glu Met
        1475                1480                1485

Val Leu Lys Val Gln Ala Phe Asn Glu Arg Thr Glu Glu Arg Val
        1490                1495                1500

Ala Glu Ala Asp Ala His Val Glu Gln Glu Thr Thr Ala Tyr Val
        1505                1510                1515

Phe Cys Gly Gln Gly Ser Gln Arg Gln Gly Met Gly Met Asp Leu
        1520                1525                1530

Tyr Val Asn Cys Pro Glu Ala Lys Ala Leu Trp Ala Arg Ala Asp
        1535                1540                1545

Lys His Leu Trp Glu Lys Tyr Gly Phe Ser Ile Leu His Ile Val
        1550                1555                1560

Gln Asn Asn Pro Pro Ala Leu Thr Val His Phe Gly Ser Gln Arg
        1565                1570                1575

Gly Arg Arg Ile Arg Ala Asn Tyr Leu Arg Met Met Gly Gln Pro
        1580                1585                1590

Pro Ile Asp Gly Arg His Pro Ile Leu Lys Gly Leu Thr Arg
        1595                1600                1605

Asn Ser Thr Ser Tyr Thr Phe Ser Tyr Ser Gln Gly Leu Leu Met
        1610                1615                1620

Ser Thr Gln Phe Ala Gln Pro Ala Leu Ala Leu Met Glu Met Ala
        1625                1630                1635

Gln Phe Glu Trp Leu Lys Ala Gln Gly Val Val Gln Lys Gly Ala
        1640                1645                1650

Arg Phe Ala Gly His Ser Leu Gly Glu Tyr Ala Ala Leu Gly Ala
        1655                1660                1665

Cys Ala Ser Phe Leu Ser Phe Glu Asp Leu Ile Ser Leu Ile Phe
        1670                1675                1680

Tyr Arg Gly Leu Lys Met Gln Asn Ala Leu Pro Arg Asp Ala Asn
        1685                1690                1695

Gly His Thr Asp Tyr Gly Met Leu Ala Ala Asp Pro Ser Arg Ile
        1700                1705                1710

Gly Lys Gly Phe Glu Glu Ala Ser Leu Lys Cys Leu Val His Ile
        1715                1720                1725

Ile Gln Gln Glu Thr Gly Trp Phe Val Glu Val Asn Tyr Asn
        1730                1735                1740

Ile Asn Ser Gln Gln Tyr Val Cys Ala Gly His Phe Arg Ala Leu
        1745                1750                1755

Trp Met Leu Gly Lys Ile Cys Asp Asp Leu Ser Cys His Pro Gln
        1760                1765                1770

Pro Glu Thr Val Glu Gly Gln Glu Leu Arg Ala Met Val Trp Lys
        1775                1780                1785

His Val Pro Thr Val Glu Gln Val Pro Arg Glu Asp Arg Met Glu
        1790                1795                1800

Arg Gly Arg Ala Thr Ile Pro Leu Pro Gly Ile Asp Ile Pro Tyr
        1805                1810                1815

His Ser Thr Met Leu Arg Gly Glu Ile Glu Pro Tyr Arg Glu Tyr
        1820                1825                1830

Leu Ser Glu Arg Ile Lys Val Gly Asp Val Lys Pro Cys Glu Leu
        1835                1840                1845

Val Gly Arg Trp Ile Pro Asn Val Val Gly Gln Pro Phe Ser Val
        1850                1855                1860
```

Asp Lys Ser Tyr Val Gln Leu Val His Gly Ile Thr Gly Ser Pro
    1865            1870                1875

Arg Leu His Ser Leu Leu Gln Gln Met Ala
    1880            1885

<210> SEQ ID NO 10
<211> LENGTH: 545
<212> TYPE: PRT
<213> ORGANISM: Cannabis sativa

<400> SEQUENCE: 10

Met Asn Cys Ser Ala Phe Ser Phe Trp Phe Val Cys Lys Ile Ile Phe
1               5                   10                  15

Phe Phe Leu Ser Phe His Ile Gln Ile Ser Ile Ala Asn Pro Arg Glu
            20                  25                  30

Asn Phe Leu Lys Cys Phe Ser Lys His Ile Pro Asn Asn Val Ala Asn
        35                  40                  45

Pro Lys Leu Val Tyr Thr Gln His Asp Gln Leu Tyr Met Ser Ile Leu
    50                  55                  60

Asn Ser Thr Ile Gln Asn Leu Arg Phe Ile Ser Asp Thr Thr Pro Lys
65              70                  75                  80

Pro Leu Val Ile Val Thr Pro Ser Asn Asn Ser His Ile Gln Ala Thr
                85                  90                  95

Ile Leu Cys Ser Lys Lys Val Gly Leu Gln Ile Arg Thr Arg Ser Gly
            100                 105                 110

Gly His Asp Ala Glu Gly Met Ser Tyr Ile Ser Gln Val Pro Phe Val
        115                 120                 125

Val Val Asp Leu Arg Asn Met His Ser Ile Lys Ile Asp Val His Ser
    130                 135                 140

Gln Thr Ala Trp Val Glu Ala Gly Ala Thr Leu Gly Glu Val Tyr Tyr
145             150                 155                 160

Trp Ile Asn Glu Lys Asn Glu Asn Leu Ser Phe Pro Gly Gly Tyr Cys
                165                 170                 175

Pro Thr Val Gly Val Gly Gly His Phe Ser Gly Gly Gly Tyr Gly Ala
            180                 185                 190

Leu Met Arg Asn Tyr Gly Leu Ala Ala Asp Asn Ile Ile Asp Ala His
        195                 200                 205

Leu Val Asn Val Asp Gly Lys Val Leu Asp Arg Lys Ser Met Gly Glu
    210                 215                 220

Asp Leu Phe Trp Ala Ile Arg Gly Gly Gly Gly Glu Asn Phe Gly Ile
225             230                 235                 240

Ile Ala Ala Trp Lys Ile Lys Leu Val Ala Val Pro Ser Lys Ser Thr
                245                 250                 255

Ile Phe Ser Val Lys Lys Asn Met Glu Ile His Gly Leu Val Lys Leu
            260                 265                 270

Phe Asn Lys Trp Gln Asn Ile Ala Tyr Lys Tyr Asp Lys Asp Leu Val
        275                 280                 285

Leu Met Thr His Phe Ile Thr Lys Asn Ile Thr Asp Asn His Gly Lys
    290                 295                 300

Asn Lys Thr Thr Val His Gly Tyr Phe Ser Ser Ile Phe His Gly Gly
305             310                 315                 320

Val Asp Ser Leu Val Asp Leu Met Asn Lys Ser Phe Pro Glu Leu Gly
                325                 330                 335

Ile Lys Lys Thr Asp Cys Lys Glu Phe Ser Trp Ile Asp Thr Thr Ile

```
                340             345             350
Phe Tyr Ser Gly Val Asn Phe Asn Thr Ala Asn Phe Lys Lys Glu
            355             360             365

Ile Leu Leu Asp Arg Ser Ala Gly Lys Lys Thr Ala Phe Ser Ile Lys
        370             375             380

Leu Asp Tyr Val Lys Lys Pro Ile Pro Glu Thr Ala Met Val Lys Ile
385             390             395             400

Leu Glu Lys Leu Tyr Glu Glu Asp Val Gly Ala Gly Met Tyr Val Leu
                405             410             415

Tyr Pro Tyr Gly Gly Ile Met Glu Glu Ile Ser Glu Ser Ala Ile Pro
            420             425             430

Phe Pro His Arg Ala Gly Ile Met Tyr Glu Leu Trp Tyr Thr Ala Ser
            435             440             445

Trp Glu Lys Gln Glu Asp Asn Glu Lys His Ile Asn Trp Val Arg Ser
        450             455             460

Val Tyr Asn Phe Thr Thr Pro Tyr Val Ser Gln Asn Pro Arg Leu Ala
465             470             475             480

Tyr Leu Asn Tyr Arg Asp Leu Asp Leu Gly Lys Thr Asn His Ala Ser
                485             490             495

Pro Asn Asn Tyr Thr Gln Ala Arg Ile Trp Gly Glu Lys Tyr Phe Gly
            500             505             510

Lys Asn Phe Asn Arg Leu Val Lys Val Lys Thr Lys Val Asp Pro Asn
            515             520             525

Asn Phe Phe Arg Asn Glu Gln Ser Ile Pro Pro Leu Pro Pro His His
            530             535             540

His
545

<210> SEQ ID NO 11
<211> LENGTH: 544
<212> TYPE: PRT
<213> ORGANISM: Cannabis sativa

<400> SEQUENCE: 11

Met Lys Cys Ser Thr Phe Ser Phe Trp Phe Val Cys Lys Ile Ile Phe
1               5               10              15

Phe Phe Phe Ser Phe Asn Ile Gln Thr Ser Ile Ala Asn Pro Arg Glu
            20              25              30

Asn Phe Leu Lys Cys Phe Ser Gln Tyr Ile Pro Asn Asn Ala Thr Asn
        35              40              45

Leu Lys Leu Val Tyr Thr Gln Asn Asn Pro Leu Tyr Met Ser Val Leu
50              55              60

Asn Ser Thr Ile His Asn Leu Arg Phe Thr Ser Asp Thr Thr Pro Lys
65              70              75              80

Pro Leu Val Ile Val Thr Pro Ser His Val Ser His Ile Gln Gly Thr
                85              90              95

Ile Leu Cys Ser Lys Lys Val Gly Leu Gln Ile Arg Thr Arg Ser Gly
            100             105             110

Gly His Asp Ser Glu Gly Met Ser Tyr Ile Ser Gln Val Pro Phe Val
            115             120             125

Ile Val Asp Leu Arg Asn Met Arg Ser Ile Lys Ile Asp Val His Ser
        130             135             140

Gln Thr Ala Trp Val Glu Ala Gly Ala Thr Leu Gly Glu Val Tyr Tyr
145             150             155             160
```

```
Trp Val Asn Glu Lys Asn Glu Asn Leu Ser Leu Ala Ala Gly Tyr Cys
                165                 170                 175
Pro Thr Val Cys Ala Gly Gly His Phe Gly Gly Gly Tyr Gly Pro
            180                 185                 190
Leu Met Arg Asn Tyr Gly Leu Ala Ala Asp Asn Ile Ile Asp Ala His
            195                 200                 205
Leu Val Asn Val His Gly Lys Val Leu Asp Arg Lys Ser Met Gly Glu
210                 215                 220
Asp Leu Phe Trp Ala Leu Arg Gly Gly Gly Ala Glu Ser Phe Gly Ile
225                 230                 235                 240
Ile Val Ala Trp Lys Ile Arg Leu Val Ala Val Pro Lys Ser Thr Met
                245                 250                 255
Phe Ser Val Lys Lys Ile Met Glu Ile His Glu Leu Val Lys Leu Val
                260                 265                 270
Asn Lys Trp Gln Asn Ile Ala Tyr Lys Tyr Asp Lys Asp Leu Leu Leu
                275                 280                 285
Met Thr His Phe Ile Thr Arg Asn Ile Thr Asp Asn Gln Gly Lys Asn
            290                 295                 300
Lys Thr Ala Ile His Thr Tyr Phe Ser Ser Val Phe Leu Gly Gly Val
305                 310                 315                 320
Asp Ser Leu Val Asp Leu Met Asn Lys Ser Phe Pro Glu Leu Gly Ile
                325                 330                 335
Lys Lys Thr Asp Cys Arg Gln Leu Ser Trp Ile Asp Thr Ile Ile Phe
            340                 345                 350
Tyr Ser Gly Val Val Asn Tyr Asp Thr Asp Asn Phe Asn Lys Glu Ile
            355                 360                 365
Leu Leu Asp Arg Ser Ala Gly Gln Asn Gly Ala Phe Lys Ile Lys Leu
            370                 375                 380
Asp Tyr Val Lys Lys Pro Ile Pro Glu Ser Val Phe Val Gln Ile Leu
385                 390                 395                 400
Glu Lys Leu Tyr Glu Glu Asp Ile Gly Ala Gly Met Tyr Ala Leu Tyr
                405                 410                 415
Pro Tyr Gly Gly Ile Met Asp Glu Ile Ser Glu Ser Ala Ile Pro Phe
            420                 425                 430
Pro His Arg Ala Gly Ile Leu Tyr Glu Leu Trp Tyr Ile Cys Ser Trp
            435                 440                 445
Glu Lys Gln Glu Asp Asn Glu Lys His Leu Asn Trp Ile Arg Asn Ile
            450                 455                 460
Tyr Asn Phe Met Thr Pro Tyr Val Ser Lys Asn Pro Arg Leu Ala Tyr
465                 470                 475                 480
Leu Asn Tyr Arg Asp Leu Asp Ile Gly Ile Asn Asp Pro Lys Asn Pro
                485                 490                 495
Asn Asn Tyr Thr Gln Ala Arg Ile Trp Gly Glu Lys Tyr Phe Gly Lys
            500                 505                 510
Asn Phe Asp Arg Leu Val Lys Val Lys Thr Leu Val Asp Pro Asn Asn
            515                 520                 525
Phe Phe Arg Asn Glu Gln Ser Ile Pro Pro Leu Pro Arg His Arg His
            530                 535                 540
```

<210> SEQ ID NO 12
<211> LENGTH: 1635
<212> TYPE: DNA
<213> ORGANISM: Cannabis sativa

<400> SEQUENCE: 12

-continued

```
atgaattgct caacattctc cttttggttt gtttgcaaaa taatattttt ctttctctca        60
ttcaatatcc aaatttcaat agctaatcct caagaaaact tccttaaatg cttctcggaa       120
tatattccta acaatccagc aaatccaaaa tcatataca ctcaacacga ccaattgtat        180
atgtctgtcc tgaattcgac aatacaaaat cttagattca cctctgatac aaccccaaaa      240
ccactcgtta ttgtcactcc ttcaaatgtc tcccatatcc aggccagtat tctctgctcc      300
aagaaagttg gtttgcagat tcgaactcga agcggtggcc atgatgctga gggtttgtcc     360
tacatatctc aagtcccatt tgctatagta gacttgagaa acatgcatac ggtcaaagta     420
gatattcata gccaaactgc gtgggttgaa gccggagcta cccttggaga agtttattat     480
tggatcaatg agatgaatga aattttagt tttcctggtg ggtattgccc tactgttggc      540
gtaggtggac actttagtgg aggaggctat ggagcattga tgcgaaatta tggccttgcg    600
gctgataata tcattgatgc acacttagtc aatgttgatg aaaagttct agatcgaaaa      660 tccatgggag aagatctatt tgggctata cgtggtggag gaggagaaaa ctttggaatc       720
attgcagcat gtaaaatcaa acttgttgtt gtcccatcaa aggctactat attcagtgtt    780
aaaaagaaca tggagataca tgggcttgtc aagttattta acaaatgcaa aaatattgct      840
tacaagtatg acaaagattt aatgctcacg actcacttca gaactaggaa tattacagat     900
aatcatggga agaataagac tacagtacat ggttacttct cttccatttt tcttggtgga     960
gtggatagtc tagttgactt gatgaacaag agctttcctg agttgggtat taaaaaaact    1020
gattgcaaag aattgagctg gattgataca accatcttct acagtggtgt tgtaaattac    1080
aacactgcta attttaaaaa ggaaattttg cttgatagat cagctgggaa gaagacggct    1140
ttctcaatta agttagacta tgttaagaaa ctaatacctg aaactgcaat ggtcaaaatt    1200
ttggaaaaat tatatgaaga agaggtagga gttgggatgt atgtgttgta cccttacggt    1260
ggtataatgg atgagatttc agaatcagca attccattcc ctcatcgagc tggaataatg   1320
tatgaacttt ggtacactgc tacctgggag aagcaagaag ataacgaaaa gcatataaac    1380
tgggttcgaa gtgtttataa tttcacaact ccttatgtgt cccaaaatcc aagattggcg    1440
tatctcaatt atagggacct tgatttagga aaaactaatc ctgagagtcc taataattac   1500
acacaagcac gtatttgggg tgaaaagtat tttggtaaaa attttaacag gttagttaag    1560
gtgaaaacca agctgatcc caataatttt tttagaaacg aacaaagtat cccacctctt    1620
ccaccgcgtc atcat                                                       1635
```

<210> SEQ ID NO 13
<211> LENGTH: 530
<212> TYPE: PRT
<213> ORGANISM: Cannabis sativa

<400> SEQUENCE: 13

```
Met Asn Cys Ser Thr Phe Ser Phe Trp Phe Val Cys Lys Ile Ile Phe
1               5                   10                  15

Phe Phe Leu Ser Phe Asn Ile Gln Ile Ser Ile Ala Asn Pro Gln Glu
            20                  25                  30

Asn Phe Leu Lys Cys Phe Ser Glu Tyr Ile Pro Asn Asn Pro Ala Pro
        35                  40                  45

Lys Phe Ile Tyr Thr Gln His Asp Gln Leu Tyr Met Ser Val Leu Asn
    50                  55                  60

Ser Thr Ile Gln Asn Leu Arg Phe Thr Ser Asp Thr Thr Pro Lys Pro
65                  70                  75                  80
```

```
Leu Val Ile Val Thr Pro Ser Asn Val Ser His Ile Gln Ala Ser Ile
                85                  90                  95
Leu Cys Ser Lys Val Gly Leu Gln Ile Arg Thr Arg Ser Gly Gly His
            100                 105                 110
Asp Ala Glu Gly Leu Ser Tyr Ile Ser Gln Val Pro Phe Ala Ile Val
            115                 120                 125
Asp Leu Arg Asn Met His Thr Val Val Asp Ile His Ser Gln Thr Ala
        130                 135                 140
Val Glu Ala Gly Ala Thr Leu Gly Glu Val Tyr Tyr Trp Ile Asn Glu
145                 150                 155                 160
Met Asn Glu Asn Phe Ser Phe Pro Gly Gly Tyr Cys Pro Thr Val Gly
                165                 170                 175
Val Gly Gly His Phe Ser Gly Gly Gly Tyr Gly Ala Leu Met Arg Asn
            180                 185                 190
Tyr Gly Leu Ala Ala Asp Asn Ile Ile Asp Ala His Leu Val Asn Val
            195                 200                 205
Asp Gly Lys Val Leu Asp Arg Lys Ser Met Gly Glu Asp Leu Phe Trp
        210                 215                 220
Ala Ile Arg Gly Gly Gly Glu Asn Phe Gly Ile Ile Ala Ala Cys
225                 230                 235                 240
Ile Lys Leu Trp Val Pro Ser Lys Ala Thr Ile Phe Ser Val Lys Lys
                245                 250                 255
Asn Met Glu Ile His Gly Leu Val Lys Leu Phe Asn Lys Trp Gln Asn
            260                 265                 270
Ile Ala Tyr Tyr Asp Lys Asp Leu Met Leu Thr Thr His Phe Arg Thr
        275                 280                 285
Arg Asn Ile Thr Asp Asn His Gly Asn Lys Thr Thr Val His Gly Tyr
        290                 295                 300
Phe Ser Ser Ile Phe Leu Gly Gly Val Asp Ser Leu Val Asp Leu Met
305                 310                 315                 320
Asn Lys Ser Phe Pro Glu Leu Gly Ile Lys Thr Asp Cys Lys Glu Leu
                325                 330                 335
Ser Trp Ile Asp Thr Thr Ile Phe Tyr Ser Gly Trp Tyr Asn Thr Ala
            340                 345                 350
Phe Lys Lys Glu Ile Leu Leu Asp Arg Ser Ala Gly Lys Lys Thr Ala
        355                 360                 365
Phe Ser Ile Lys Leu Asp Tyr Val Lys Lys Leu Ile Pro Glu Thr Ala
        370                 375                 380
Met Val Lys Ile Leu Glu Leu Tyr Glu Glu Val Gly Val Gly Met
385                 390                 395                 400
Tyr Val Leu Tyr Pro Tyr Gly Gly Ile Met Asp Glu Ile Ser Glu Ser
                405                 410                 415
Ala Ile Pro Phe Pro His Arg Ala Gly Ile Met Tyr Glu Leu Tyr Thr
            420                 425                 430
Ala Thr Glu Lys Gln Glu Asp Asn Glu Lys His Ile Asn Trp Val Arg
        435                 440                 445
Ser Val Tyr Asn Phe Thr Thr Pro Tyr Val Ser Gln Asn Pro Arg Leu
        450                 455                 460
Ala Tyr Leu Asn Tyr Arg Asp Leu Asp Leu Gly Lys Thr Asn Pro Glu
465                 470                 475                 480
Ser Pro Asn Asn Tyr Thr Gln Ala Arg Ile Trp Gly Glu Lys Tyr Phe
                485                 490                 495
```

Gly Lys Asn Phe Asn Arg Leu Val Lys Val Lys Thr Lys Ala Asp Pro
            500                 505                 510

Asn Asn Phe Phe Arg Asn Glu Gln Ser Ile Pro Pro Leu Pro Pro Arg
        515                 520                 525

His His
    530

<210> SEQ ID NO 14
<211> LENGTH: 924
<212> TYPE: DNA
<213> ORGANISM: Artificial
<220> FEATURE:
<223> OTHER INFORMATION: NphB-Gen, Codon-optimiert fur E. coli

<400> SEQUENCE: 14

```
atgagcgaag ctgcggatgt tgaacgcgtg tatgcggcaa tggaagaggc agcaggcctc      60
ttaggtgtgg cttgtgcgcg tgataaaatc tacccgttac tgagcacctt tcaggatacg     120
ctggtggaag tggttccgt ggtagtgttc tcaatggcat ccggtcgtca cagtaccgaa      180
ctggacttca gcatttcagt cccgacatcg catggagatc cgtatgcgac cgtagtcgag     240
aaaggcctgt ttccggccac tggccatcct gtggatgacc tgttggccga tacccagaaa     300
catctcccag taagcatgtt tgccattgac ggcgaagtga ctggcggctt caagaaaacc     360
tacgcgttct ttccgacaga taacatgcca ggagttgcgg aactgagcgc gattccgtcc     420
atgccgcctg ctgttgcaga gaatgccgaa ctctttgccc gttatgggct ggacaaagtc     480
cagatgacga gtatggacta taagaaacgc caggtcaacc tgtacttcag tgaactgagt     540
gcgcaaacct tggaagctga atcggtgctg gcccttgttc gtgagctggg tctgcatgtt     600
ccaaacgaat gggtctgaa attttgcaaa cggagctttt cggtgtatcc cacgctgaat      660
tgggaaacag gcaagatcga tcgcttgtgc tttgccgtta tctcgaatga tcctacccct     720
gtaccctctt cagacgaagg ggatattgag aaattccaca actatgcaac taaagcgccg     780
tatgcttatg ttggcgaaaa cgcacgttta gtgtacggcc ttacgctctc tccgaaagaa     840
gagtactaca aactgggtgc gtattaccac attaccgatg tccaacgcgg gttactgaaa     900
gcctttgact ctctggagga ttaa                                            924
```

<210> SEQ ID NO 15
<211> LENGTH: 924
<212> TYPE: DNA
<213> ORGANISM: Artificial
<220> FEATURE:
<223> OTHER INFORMATION: NphB-Gen, Codon-harmonisiert fur S. cerevisiae

<400> SEQUENCE: 15

```
atgtctgaag cggcggacgt tgaaagagtt tatgctgcta tggaagaagc tgcggggttg      60
ttgggggttg cttgtgcgag agataagata tatccattat tgtccacctt ccaagacacc     120
ttggttgaag tggttctgt tgttgttttt tctatggctt ctgggcggca ctctacggaa      180
ttggattttt ctatttctgt tccaacctcc catggtgatc catatgctac tgttgttgaa     240
aaagggttgt ttccagctac tggtcatcca gttgatgatt tgttggctga tactcaaaaa     300
catctccccgg tatctatgtt cgctattgat ggtgaagtta ctggtggttt caaaaagact    360
tacgcttttct tcccaactga taacatgcca ggtgttgctg aattgtctgc tattccatct    420
atgccaccag ctgttgcaga aaatgctgaa ttatttgcta gatacgggtt ggacaaggtt    480
caaatgactt ctatggatta caagaagaga caagtcaact tgtacttctc gaattgtca     540
```

```
gctcaaactt tggaagctga atctgttttg ctttggttta gagaattggg tttacacgtt        600
ccaaacgaat taggtttgaa gttctgcaag agatccttct ctgtttaccc aactttgaat        660
tgggaaaccg gtaaaattga tcggttgtgc tttgccgtta tttccaatga tccaactttg        720
gttccatcct ctgatgaagg tgatatcgaa aagtttcata actacgctac taaggctcca        780
tacgcttatg ttggtgaaaa gagaacttta gtttacgggc tcactttgtc cccaaaagaa        840
gaatattaca agttgggtgc ctactaccat atcactgatg ttcaacgggg gctcttgaag        900
gcttttgatt ctttggaaga ttga                                              924

<210> SEQ ID NO 16
<211> LENGTH: 924
<212> TYPE: DNA
<213> ORGANISM: Artificial
<220> FEATURE:
<223> OTHER INFORMATION: NphB-Gen, Codon-harmonisiert fur S.cerevisiae,
      Basenaustausch 883-885 (CAT)

<400> SEQUENCE: 16
atgtctgaag cggcggacgt tgaaagagtt tatgctgcta tggaagaagc tgcggggttg        60 ttggggttg cttgtgcgag agataagata tatccattat tgtccacctt ccaagacacc        120
ttggttgaag gtggttctgt tgttgttttt tctatggctt ctgggcggca ctctacggaa        180 ttggatttt ctatttctgt tccaacctcc catggtgatc catatgctac tgttgttgaa        240
aaagggttgt ttccagctac tggtcatcca gttgatgatt tgttggctga tactcaaaaa        300
catctcccgg tatctatgtt cgctattgat ggtgaagtta ctggtggttt caaaaagact        360
tacgctttct tcccaactga taacatgcca ggtgttgctg aattgtctgc tattccatct        420
atgccaccag ctgttgcaga aaatgctgaa ttatttgcta gatacgggtt ggacaaggtt        480
caaatgactt ctatggatta caagaagaga caagtcaact tgtacttctc cgaattgtca        540
gctcaaactt tggaagctga atctgttttg ctttggttta gagaattggg tttacacgtt        600
ccaaacgaat taggtttgaa gttctgcaag agatccttct ctgtttaccc aactttgaat        660
tgggaaaccg gtaaaattga tcggttgtgc tttgccgtta tttccaatga tccaactttg        720
gttccatcct ctgatgaagg tgatatcgaa aagtttcata actacgctac taaggctcca        780
tacgcttatg ttggtgaaaa gagaacttta gtttacgggc tcactttgtc cccaaaagaa        840
gaatattaca agttgggtgc ctactaccat atcactgatg ttcatcgggg gctcttgaag        900
gcttttgatt ctttggaaga ttga                                              924

<210> SEQ ID NO 17
<211> LENGTH: 307
<212> TYPE: PRT
<213> ORGANISM: Artificial
<220> FEATURE:
<223> OTHER INFORMATION: modifizierte Prenyltransferase,
      Aminosaureaustausch Q295H

<400> SEQUENCE: 17

Met Ser Glu Ala Ala Asp Val Glu Arg Val Tyr Ala Ala Met Glu Glu
1               5                  10                  15

Ala Ala Gly Leu Leu Gly Val Ala Cys Ala Arg Asp Lys Ile Tyr Pro
            20                  25                  30

Leu Leu Ser Thr Phe Gln Asp Thr Leu Val Glu Gly Gly Ser Val Val
        35                  40                  45

Val Phe Ser Met Ala Ser Gly Arg His Ser Thr Glu Leu Asp Phe Ser
    50                  55                  60
```

Ile Ser Val Pro Thr Ser His Gly Asp Pro Tyr Ala Thr Val Val Glu
65                  70                  75                  80

Lys Gly Leu Phe Pro Ala Thr Gly His Pro Val Asp Asp Leu Leu Ala
                85                  90                  95

Asp Thr Gln Lys His Leu Pro Val Ser Met Phe Ala Ile Asp Gly Glu
            100                 105                 110

Val Thr Gly Gly Phe Lys Lys Thr Tyr Ala Phe Phe Pro Thr Asp Asn
        115                 120                 125

Met Pro Gly Val Ala Glu Leu Ser Ala Ile Pro Ser Met Pro Pro Ala
130                 135                 140

Val Ala Glu Asn Ala Glu Leu Phe Ala Arg Tyr Gly Leu Asp Lys Val
145                 150                 155                 160

Gln Met Thr Ser Met Asp Tyr Lys Lys Arg Gln Val Asn Leu Tyr Phe
                165                 170                 175

Ser Glu Leu Ser Ala Gln Thr Leu Glu Ala Glu Ser Val Leu Ala Leu
            180                 185                 190

Val Arg Glu Leu Gly Leu His Val Pro Asn Glu Leu Gly Leu Lys Phe
        195                 200                 205

Cys Lys Arg Ser Phe Ser Val Tyr Pro Thr Leu Asn Trp Glu Thr Gly
210                 215                 220

Lys Ile Asp Arg Leu Cys Phe Ala Val Ile Ser Asn Asp Pro Thr Leu
225                 230                 235                 240

Val Pro Ser Ser Asp Glu Gly Asp Ile Glu Lys Phe His Asn Tyr Ala
                245                 250                 255

Thr Lys Ala Pro Tyr Ala Tyr Val Gly Glu Lys Arg Thr Leu Val Tyr
            260                 265                 270

Gly Leu Thr Leu Ser Pro Lys Glu Glu Tyr Tyr Lys Leu Gly Ala Tyr
        275                 280                 285

Tyr His Ile Thr Asp Val His Arg Gly Leu Leu Lys Ala Phe Asp Ser
    290                 295                 300

Leu Glu Asp
305

<210> SEQ ID NO 18
<211> LENGTH: 924
<212> TYPE: DNA
<213> ORGANISM: Artificial
<220> FEATURE:
<223> OTHER INFORMATION: NphB-Gen, Codon-harmonisiert fur S. cerevisiae,
      Basenaustausch 883-885 (TTG)

<400> SEQUENCE: 18
atgtctgaag cggcggacgt tgaaagagtt tatgctgcta tggaagaagc tgcggggttg      60
ttgggggttg cttgtgcgag agataagata tatccattat tgtccacctt ccaagacacc     120
ttggttgaag tggttctgt tgttgttttt tctatggctt ctgggcggca ctctacggaa      180
ttggattttt ctatttctgt tccaacctcc catggtgatc catatgctac tgttgttgaa     240
aaagggttgt ttccagctac tggtcatcca gttgatgatt tgttggctga tactcaaaaa     300 catctccccgg tatctatgtt cgctattgat ggtgaagtta ctggtggttt caaaaagact    360
tacgctttct tcccaactga taacatgcca ggtgttgctg aattgtctgc tattccatct     420
atgccaccag ctgttgcaga aaatgctgaa ttatttgcta gatacgggtt ggacaaggtt    480
caaatgactt ctatggatta caagaagaga caagtcaact tgtacttctc gaattgtca     540 gctcaaactt tggaagctga atctgttttg gctttggtta gagaattggg tttacacgtt    600

```
ccaaacgaat taggtttgaa gttctgcaag agatccttct ctgtttaccc aactttgaat    660
tgggaaaccg gtaaaattga tcggttgtgc tttgccgtta tttccaatga tccaactttg    720
gttccatcct ctgatgaagg tgatatcgaa aagtttcata actacgctac taaggctcca    780
tacgcttatg ttggtaaaaa agaaacttta gtttacgggc tcactttgtc cccaaaagaa    840
gaatattaca agttgggtgc ctactaccat atcactgatg ttttgcgggg gctcttgaag    900
gcttttgatt ctttggaaga ttga                                          924
```

<210> SEQ ID NO 19
<211> LENGTH: 307
<212> TYPE: PRT
<213> ORGANISM: Artificial
<220> FEATURE:
<223> OTHER INFORMATION: modifizierte Prenyltransferase,
      Aminosaureaustausch Q295L

<400> SEQUENCE: 19

```
Met Ser Glu Ala Ala Asp Val Glu Arg Val Tyr Ala Ala Met Glu Glu
1               5                   10                  15

Ala Ala Gly Leu Leu Gly Val Ala Cys Ala Arg Asp Lys Ile Tyr Pro
            20                  25                  30

Leu Leu Ser Thr Phe Gln Asp Thr Leu Val Glu Gly Gly Ser Val Val
        35                  40                  45

Val Phe Ser Met Ala Ser Gly Arg His Ser Thr Glu Leu Asp Phe Ser
    50                  55                  60

Ile Ser Val Pro Thr Ser His Gly Asp Pro Tyr Ala Thr Val Val Glu
65                  70                  75                  80

Lys Gly Leu Phe Pro Ala Thr Gly His Pro Val Asp Asp Leu Leu Ala
                85                  90                  95

Asp Thr Gln Lys His Leu Pro Val Ser Met Phe Ala Ile Asp Gly Glu
            100                 105                 110

Val Thr Gly Gly Phe Lys Lys Thr Tyr Ala Phe Pro Thr Asp Asn
        115                 120                 125

Met Pro Gly Val Ala Glu Leu Ser Ala Ile Pro Ser Met Pro Pro Ala
    130                 135                 140

Val Ala Glu Asn Ala Glu Leu Phe Ala Arg Tyr Gly Leu Asp Lys Val
145                 150                 155                 160

Gln Met Thr Ser Met Asp Tyr Lys Lys Arg Gln Val Asn Leu Tyr Phe
                165                 170                 175

Ser Glu Leu Ser Ala Gln Thr Leu Glu Ala Glu Ser Val Leu Ala Leu
            180                 185                 190

Val Arg Glu Leu Gly Leu His Val Pro Asn Glu Leu Gly Leu Lys Phe
        195                 200                 205

Cys Lys Arg Ser Phe Ser Val Tyr Pro Thr Leu Asn Trp Glu Thr Gly
    210                 215                 220

Lys Ile Asp Arg Leu Cys Phe Ala Val Ile Ser Asn Asp Pro Thr Leu
225                 230                 235                 240

Val Pro Ser Ser Asp Glu Gly Asp Ile Glu Lys Phe His Asn Tyr Ala
                245                 250                 255

Thr Lys Ala Pro Tyr Ala Tyr Val Gly Glu Lys Arg Thr Leu Val Tyr
            260                 265                 270

Gly Leu Thr Leu Ser Pro Lys Glu Glu Tyr Tyr Lys Leu Gly Ala Tyr
        275                 280                 285

Tyr His Ile Thr Asp Val Leu Arg Gly Leu Leu Lys Ala Phe Asp Ser
```

290                 295                 300

Leu Glu Asp
305

<210> SEQ ID NO 20
<211> LENGTH: 586
<212> TYPE: PRT
<213> ORGANISM: Saccharomyces cerevisiae (Stamm ATCC 204508 / S288c)

<400> SEQUENCE: 20

Met Ser Arg Ser Asn Ser Ile Tyr Thr Glu Asp Ile Glu Met Tyr Pro
1               5                   10                  15

Thr His Asn Glu Gln His Leu Thr Arg Glu Tyr Thr Lys Pro Asp Gly
            20                  25                  30

Gln Thr Lys Ser Glu Lys Leu Asn Phe Glu Gly Ala Tyr Ile Asn Ser
        35                  40                  45

His Gly Thr Leu Ser Lys Thr Thr Arg Glu Ile Glu Gly Asp Leu
    50                  55                  60

Asp Ser Glu Thr Ser Ser His Ser Ser Asp Asp Lys Val Asp Pro Thr
65                  70                  75                  80

Gln Gln Ile Thr Ala Glu Thr Lys Ala Pro Tyr Thr Leu Leu Ser Tyr
                85                  90                  95

Gly Gln Lys Trp Gly Met Val Ala Ile Leu Thr Met Cys Gly Phe Trp
            100                 105                 110

Ser Ser Leu Gly Ser Pro Ile Tyr Tyr Pro Ala Leu Arg Gln Leu Glu
        115                 120                 125

Lys Gln Phe Asn Val Asp Glu Asn Met Val Asn Val Thr Val Val Val
130                 135                 140

Tyr Leu Leu Phe Gln Gly Ile Ser Pro Thr Val Ser Gly Gly Leu Ala
145                 150                 155                 160

Asp Cys Phe Gly Arg Arg Pro Ile Ile Leu Ala Gly Met Leu Ile Tyr
                165                 170                 175

Val Ile Ala Ser Ile Gly Leu Ala Cys Ala Pro Ser Tyr Gly Val Ile
            180                 185                 190

Ile Phe Leu Arg Cys Ile Gln Ser Ile Gly Ile Ser Pro Thr Ile Ala
        195                 200                 205

Ile Ser Ser Gly Val Val Gly Asp Phe Thr Leu Lys His Glu Arg Gly
210                 215                 220

Thr Phe Val Gly Ala Thr Ser Gly Phe Val Leu Leu Gly Gln Cys Phe
225                 230                 235                 240

Gly Ser Leu Ile Gly Ala Val Leu Thr Ala Arg Trp Asp Trp Arg Ala
                245                 250                 255

Ile Phe Trp Phe Leu Thr Ile Gly Cys Gly Ser Cys Phe Leu Ile Ala
            260                 265                 270

Phe Leu Ile Leu Pro Glu Thr Lys Arg Thr Ile Ala Gly Asn Leu Ser
        275                 280                 285

Ile Lys Pro Lys Arg Phe Ile Asn Arg Ala Pro Ile Phe Leu Leu Gly
    290                 295                 300

Pro Val Arg Arg Arg Phe Lys Tyr Asp Asn Pro Asp Tyr Glu Thr Leu
305                 310                 315                 320

Asp Pro Thr Ile Pro Lys Leu Asp Leu Ser Ser Ala Gly Lys Ile Leu
                325                 330                 335

Val Leu Pro Glu Ile Ile Leu Ser Leu Phe Pro Ser Gly Leu Leu Phe
            340                 345                 350

```
Ala Met Trp Thr Leu Met Leu Ser Ile Ser Ser Gly Leu Ser Val
        355                 360                 365

Ala Pro Tyr Asn Tyr His Leu Val Ile Ile Gly Val Cys Tyr Leu Pro
370                 375                 380

Gly Gly Ile Gly Gly Leu Met Gly Ser Phe Phe Thr Gly Arg Ile Ile
385                 390                 395                 400

Asp Met Tyr Phe Lys Arg Lys Ile Lys Lys Phe Glu Gln Asp Lys Ala
                405                 410                 415

Asn Gly Leu Ile Pro Gln Asp Ala Glu Ile Asn Met Phe Lys Val Arg
            420                 425                 430

Leu Val Cys Leu Leu Pro Gln Asn Phe Leu Ala Val Val Ala Tyr Leu
        435                 440                 445

Leu Phe Gly Trp Ser Ile Asp Lys Gly Trp Arg Ile Glu Ser Ile Leu
450                 455                 460

Ile Thr Ser Phe Val Cys Ser Tyr Cys Ala Met Ser Thr Leu Ser Thr
465                 470                 475                 480

Ser Thr Thr Leu Leu Val Asp Leu Tyr Pro Thr Lys Ser Ser Thr Ala
                485                 490                 495

Ser Ser Cys Phe Asn Phe Val Arg Cys Ser Leu Ser Thr Ile Phe Met
            500                 505                 510

Gly Cys Phe Ala Lys Met Lys Ala Ala Met Thr Val Gly Gly Thr Phe
        515                 520                 525

Thr Phe Leu Cys Ala Leu Val Phe Phe Asn Phe Leu Met Phe Ile
530                 535                 540

Pro Met Lys Tyr Gly Met Lys Trp Arg Glu Asp Arg Leu Leu Lys Gln
545                 550                 555                 560

Gln Arg Gln Ser Trp Leu Asn Thr Leu Ala Val Lys Ala Lys Lys Gly
                565                 570                 575

Thr Lys Arg Asp Gln Asn Asp Asn His Asn
                580                 585

<210> SEQ ID NO 21
<211> LENGTH: 1511
<212> TYPE: PRT
<213> ORGANISM: Saccharomyces cerevisiae (Stamm ATCC 204508 / S288c)

<400> SEQUENCE: 21

Met Ser Ser Thr Asp Glu His Ile Glu Lys Asp Ile Ser Arg Ser
1               5                   10                  15

Asn His Asp Asp Asp Tyr Ala Asn Ser Val Gln Ser Tyr Ala Ala Ser
                20                  25                  30

Glu Gly Gln Val Asp Asn Glu Asp Leu Ala Ala Thr Ser Gln Leu Ser
            35                  40                  45

Arg His Leu Ser Asn Ile Leu Ser Asn Glu Glu Gly Ile Glu Arg Leu
50                  55                  60

Glu Ser Met Ala Arg Val Ile Ser His Lys Thr Lys Lys Glu Met Asp
65                  70                  75                  80

Ser Phe Glu Ile Asn Asp Leu Asp Phe Asp Leu Arg Ser Leu Leu His
                85                  90                  95

Tyr Leu Arg Ser Arg Gln Leu Glu Gln Gly Ile Glu Pro Gly Asp Ser
                100                 105                 110

Gly Ile Ala Phe Lys Asn Leu Thr Ala Val Gly Val Asp Ala Ser Ala
            115                 120                 125

Ala Tyr Gly Pro Ser Val Glu Glu Met Phe Arg Asn Ile Ala Ser Ile
130                 135                 140
```

```
Pro Ala His Leu Ile Ser Lys Phe Thr Lys Lys Ser Asp Val Pro Leu
145                 150                 155                 160

Arg Asn Ile Ile Gln Asn Cys Thr Gly Val Val Glu Ser Gly Glu Met
            165                 170                 175

Leu Phe Val Val Gly Arg Pro Ala Gly Cys Ser Thr Phe Leu Lys
        180                 185                 190

Cys Leu Ser Gly Glu Thr Ser Glu Leu Val Asp Val Gln Gly Glu Phe
        195                 200                 205

Ser Tyr Asp Gly Leu Asp Gln Ser Glu Met Met Ser Lys Tyr Lys Gly
    210                 215                 220

Tyr Val Ile Tyr Cys Pro Glu Leu Asp Phe His Phe Pro Lys Ile Thr
225                 230                 235                 240

Val Lys Glu Thr Ile Asp Phe Ala Leu Lys Cys Lys Thr Pro Arg Val
            245                 250                 255

Arg Ile Asp Lys Met Thr Arg Lys Gln Tyr Val Asp Asn Ile Arg Asp
            260                 265                 270

Met Trp Cys Thr Val Phe Gly Leu Arg His Thr Tyr Ala Thr Lys Val
        275                 280                 285

Gly Asn Asp Phe Val Arg Gly Val Ser Gly Glu Arg Lys Arg Val
290                 295                 300

Ser Leu Val Glu Ala Gln Ala Met Asn Ala Ser Ile Tyr Ser Trp Asp
305                 310                 315                 320

Asn Ala Thr Arg Gly Leu Asp Ala Ser Thr Ala Leu Glu Phe Ala Gln
            325                 330                 335

Ala Ile Arg Thr Ala Thr Asn Met Val Asn Asn Ser Ala Ile Val Ala
        340                 345                 350

Ile Tyr Gln Ala Gly Glu Asn Ile Tyr Glu Leu Phe Asp Lys Thr Thr
        355                 360                 365

Val Leu Tyr Asn Gly Arg Gln Ile Tyr Phe Gly Pro Ala Asp Lys Ala
    370                 375                 380

Val Gly Tyr Phe Gln Arg Met Gly Trp Val Lys Pro Asn Arg Met Thr
385                 390                 395                 400

Ser Ala Glu Phe Leu Thr Ser Val Thr Val Asp Phe Glu Asn Arg Thr
            405                 410                 415

Leu Asp Ile Lys Pro Gly Tyr Glu Asp Lys Val Pro Lys Ser Ser Ser
            420                 425                 430

Glu Phe Glu Glu Tyr Trp Leu Asn Ser Glu Asp Tyr Gln Glu Leu Leu
        435                 440                 445

Arg Thr Tyr Asp Asp Tyr Gln Ser Arg His Pro Val Asn Glu Thr Arg
    450                 455                 460

Asp Arg Leu Asp Val Ala Lys Lys Gln Arg Leu Gln Gln Gly Gln Arg
465                 470                 475                 480

Glu Asn Ser Gln Tyr Val Val Asn Tyr Trp Thr Gln Val Tyr Cys
            485                 490                 495

Met Ile Arg Gly Phe Gln Arg Val Lys Gly Asp Ser Thr Tyr Thr Lys
        500                 505                 510

Val Tyr Leu Ser Ser Phe Leu Ile Lys Ala Leu Ile Ile Gly Ser Met
    515                 520                 525

Phe His Lys Ile Asp Asp Lys Ser Gln Ser Thr Thr Ala Gly Ala Tyr
    530                 535                 540

Ser Arg Gly Gly Met Leu Phe Tyr Val Leu Leu Phe Ala Ser Val Thr
545                 550                 555                 560
```

```
Ser Leu Ala Glu Ile Gly Asn Ser Phe Ser Arg Pro Val Ile Val
            565                 570                 575

Lys His Lys Ser Tyr Ser Met Tyr His Leu Ser Ala Glu Ser Leu Gln
        580                 585                 590

Glu Ile Ile Thr Glu Phe Pro Thr Lys Phe Val Ala Ile Val Ile Leu
            595                 600                 605

Cys Leu Ile Thr Tyr Trp Ile Pro Phe Met Lys Tyr Glu Ala Gly Ala
    610                 615                 620

Phe Phe Gln Tyr Ile Leu Tyr Leu Leu Thr Val Gln Gln Cys Thr Ser
625                 630                 635                 640

Phe Ile Phe Lys Phe Val Ala Thr Met Ser Lys Ser Gly Val Asp Ala
                645                 650                 655

His Ala Val Gly Gly Leu Trp Val Leu Met Leu Cys Val Tyr Ala Gly
            660                 665                 670

Phe Val Leu Pro Ile Gly Glu Met His His Trp Ile Arg Trp Leu His
        675                 680                 685

Phe Ile Asn Pro Leu Thr Tyr Ala Phe Glu Ser Leu Val Ser Thr Glu
    690                 695                 700

Phe His His Arg Glu Met Leu Cys Ser Ala Leu Val Pro Ser Gly Pro
705                 710                 715                 720

Gly Tyr Glu Gly Ile Ser Ile Ala Asn Gln Val Cys Asp Ala Ala Gly
                725                 730                 735

Ala Val Lys Gly Asn Leu Tyr Val Ser Gly Asp Ser Tyr Ile Leu His
            740                 745                 750

Gln Tyr His Phe Ala Tyr Lys His Ala Trp Arg Asn Trp Gly Val Asn
        755                 760                 765

Ile Val Trp Thr Phe Gly Tyr Ile Val Phe Asn Val Ile Leu Ser Glu
    770                 775                 780

Tyr Leu Lys Pro Val Glu Gly Gly Asp Leu Leu Leu Tyr Lys Arg
785                 790                 795                 800

Gly His Met Pro Glu Leu Gly Thr Glu Asn Ala Asp Ala Arg Thr Ala
                805                 810                 815

Ser Arg Glu Glu Met Met Glu Ala Leu Asn Gly Pro Asn Val Asp Leu
            820                 825                 830

Glu Lys Val Ile Ala Glu Lys Asp Val Phe Thr Trp Asn His Leu Asp
        835                 840                 845

Tyr Thr Ile Pro Tyr Asp Gly Ala Thr Arg Lys Leu Leu Ser Asp Val
    850                 855                 860

Phe Gly Tyr Val Lys Pro Gly Lys Met Thr Ala Leu Met Gly Glu Ser
865                 870                 875                 880

Gly Ala Gly Lys Thr Thr Leu Leu Asn Val Leu Ala Gln Arg Ile Asn
                885                 890                 895

Met Gly Val Ile Thr Gly Asp Met Leu Val Asn Ala Lys Pro Leu Pro
            900                 905                 910

Ala Ser Phe Asn Arg Ser Cys Gly Tyr Val Ala Gln Ala Asp Asn His
        915                 920                 925

Met Ala Glu Leu Ser Val Arg Glu Ser Leu Arg Phe Ala Ala Glu Leu
    930                 935                 940

Arg Gln Gln Ser Ser Val Pro Leu Glu Glu Lys Tyr Glu Tyr Val Glu
945                 950                 955                 960

Lys Ile Ile Thr Leu Leu Gly Met Gln Asn Tyr Ala Glu Ala Leu Val
                965                 970                 975

Gly Lys Thr Gly Arg Gly Leu Asn Val Glu Gln Arg Lys Lys Leu Ser
```

-continued

```
              980             985              990
Ile Gly Val Glu Leu Val Ala Lys Pro Ser Leu Leu Leu Phe Leu Asp
        995            1000             1005
Glu Pro Thr Ser Gly Leu Asp Ser Gln Ser Ala Trp Ser Ile Val
   1010            1015            1020
Gln Phe Met Arg Ala Leu Ala Asp Ser Gly Gln Ser Ile Leu Cys
   1025            1030            1035
Thr Ile His Gln Pro Ser Ala Thr Leu Phe Glu Gln Phe Asp Arg
   1040            1045            1050
Leu Leu Leu Leu Lys Lys Gly Gly Lys Met Val Tyr Phe Gly Asp
   1055            1060            1065
Ile Gly Pro Asn Ser Glu Thr Leu Leu Lys Tyr Phe Glu Arg Gln
   1070            1075            1080
Ser Gly Met Lys Cys Gly Val Ser Glu Asn Pro Ala Glu Tyr Ile
   1085            1090            1095
Leu Asn Cys Ile Gly Ala Gly Ala Thr Ala Ser Val Asn Ser Asp
   1100            1105            1110
Trp His Asp Leu Trp Leu Ala Ser Pro Glu Cys Ala Ala Ala Arg
   1115            1120            1125
Ala Glu Val Glu Glu Leu His Arg Thr Leu Pro Gly Arg Ala Val
   1130            1135            1140
Asn Asp Asp Pro Glu Leu Ala Thr Arg Phe Ala Ala Ser Tyr Met
   1145            1150            1155
Thr Gln Ile Lys Cys Val Leu Arg Arg Thr Ala Leu Gln Phe Trp
   1160            1165            1170
Arg Ser Pro Val Tyr Ile Arg Ala Lys Phe Phe Glu Cys Val Ala
   1175            1180            1185
Cys Ala Leu Phe Val Gly Leu Ser Tyr Val Gly Val Asn His Ser
   1190            1195            1200
Val Gly Gly Ala Ile Glu Ala Phe Ser Ser Ile Phe Met Leu Leu
   1205            1210            1215
Leu Ile Ala Leu Ala Met Ile Asn Gln Leu His Val Phe Ala Tyr
   1220            1225            1230
Asp Ser Arg Glu Leu Tyr Glu Val Arg Glu Ala Ala Ser Asn Thr
   1235            1240            1245
Phe His Trp Ser Val Leu Leu Leu Cys His Ala Ala Val Glu Asn
   1250            1255            1260
Phe Trp Ser Thr Leu Cys Gln Phe Met Cys Phe Ile Cys Tyr Tyr
   1265            1270            1275
Trp Pro Ala Gln Phe Ser Gly Arg Ala Ser His Ala Gly Phe Phe
   1280            1285            1290
Phe Phe Phe Tyr Val Leu Ile Phe Pro Leu Tyr Phe Val Thr Tyr
   1295            1300            1305
Gly Leu Trp Ile Leu Tyr Met Ser Pro Asp Val Pro Ser Ala Ser
   1310            1315            1320
Met Ile Asn Ser Asn Leu Phe Ala Ala Met Leu Leu Phe Cys Gly
   1325            1330            1335
Ile Leu Gln Pro Arg Glu Lys Met Pro Ala Phe Trp Arg Arg Leu
   1340            1345            1350
Met Tyr Asn Val Ser Pro Phe Thr Tyr Val Val Gln Ala Leu Val
   1355            1360            1365
Thr Pro Leu Val His Asn Lys Lys Val Val Cys Asn Pro His Glu
   1370            1375            1380
```

```
Tyr Asn Ile Met Asp Pro Pro Ser Gly Lys Thr Cys Gly Glu Phe
        1385                1390                1395

Leu Ser Thr Tyr Met Asp Asn Asn Thr Gly Tyr Leu Val Asn Pro
    1400                1405                1410

Thr Ala Thr Glu Asn Cys Gln Tyr Cys Pro Tyr Thr Val Gln Asp
        1415                1420                1425

Gln Val Val Ala Lys Tyr Asn Val Lys Trp Asp His Arg Trp Arg
    1430                1435                1440

Asn Phe Gly Phe Met Trp Ala Tyr Ile Cys Phe Asn Ile Ala Ala
        1445                1450                1455

Met Leu Ile Cys Tyr Tyr Val Val Arg Val Lys Val Trp Ser Leu
    1460                1465                1470

Lys Ser Val Leu Asn Phe Lys Lys Trp Phe Asn Gly Pro Arg Lys
        1475                1480                1485

Glu Arg His Glu Lys Asp Thr Asn Ile Phe Gln Thr Val Pro Gly
    1490                1495                1500

Asp Glu Asn Lys Ile Thr Lys Lys
        1505                1510

<210> SEQ ID NO 22
<211> LENGTH: 927
<212> TYPE: DNA
<213> ORGANISM: Artificial
<220> FEATURE:
<223> OTHER INFORMATION: NphB-Gen, Codon-optimiert fur E. coli,
      Basenaustausch 883-885 (CAT)

<400> SEQUENCE: 22
atgagcgaag ctgcggatgt tgaacgcgtg tatgcggcaa tggaagaggc agcaggcctc      60
ttaggtgtgg cttgtgcgcg tgataaaatc tacccgttac tgagcaccct tcaggatacg     120
ctggtggaag tggttccgt ggtagtgttc tcaatggcat ccggtcgtca cagtaccgaa      180
ctggacttca gcatttcagt cccgacatcg catggagatc cgtatgcgac cgtagtcgag     240
aaaggcctgt ttccggccac tggccatcct gtggatgacc tgttggccga tacccagaaa     300
catctcccag taagcatgtt tgccattgac ggcgaagtga ctggcggctt caagaaaacc     360
tacgcgttct ttccgacaga taacatgcca ggagttgcgg aactgagcgc gattccgtcc     420
atgccgcctg ctgttgcaga gaatgccgaa ctctttgccc gttatgggct ggacaaagtc     480
cagatgacga gtatggacta taagaaacgc caggtcaacc tgtacttcag tgaactgagt     540
gcgcaaacct tggaagctga atcggtgctg gcccttgttc gtgagctggg tctgcatgtt     600
ccaaacgaat tgggtctgaa attttgcaaa cggagctttt cggtgtatcc cacgctgaat     660
tgggaaacag gcaagatcga tcgcttgtgc tttgccgtta tctcgaatga tcctacccttt    720 gtaccctctt cagacgaagg ggatattgag aaattccaca actatgcaac taaagcgccg    780
tatgcttatg ttggcgaaaa gcgcacgtta gtgtacggcc ttacgctctc tccgaaagaa    840
gagtactaca aactgggtgc gtattaccac attaccgatg tccatcgcgg gttactgaaa     900
gcctttgact ctctggagga ttaatga                                         927

<210> SEQ ID NO 23
<211> LENGTH: 927
<212> TYPE: DNA
<213> ORGANISM: Artificial
<220> FEATURE:
<223> OTHER INFORMATION: NphB-Gen, Codon-optimiert fur E.coli,
      Basenaustausch 883-885 (CTG)
```

<400> SEQUENCE: 23

```
atgagcgaag ctgcggatgt tgaacgcgtg tatgcggcaa tggaagaggc agcaggcctc      60
ttaggtgtgg cttgtgcgcg tgataaaatc tacccgttac tgagcacctt tcaggatacg     120
ctggtggaag gtggttccgt ggtagtgttc tcaatggcat ccggtcgtca cagtaccgaa     180
ctggacttca gcatttcagt cccgacatcg catggagatc cgtatgcgac cgtagtcgag     240
aaaggcctgt ttccggccac tggccatcct gtggatgacc tgttggccga tacccagaaa     300
catctcccag taagcatgtt tgccattgac ggcgaagtga ctggcggctt caagaaaacc     360
tacgcgttct ttccgacaga taacatgcca ggagttgcgg aactgagcgc gattccgtcc     420
atgccgcctg ctgttgcaga gaatgccgaa ctctttgccc gttatgggct ggacaaagtc     480
cagatgacga gtatggacta taagaaacgc aggtcaacc tgtacttcag tgaactgagt      540
gcgcaaacct tggaagctga atcggtgctg gcccttgttc gtgagctggg tctgcatgtt     600
ccaaacgaat gggtctgaa attttgcaaa cggagctttt cggtgtatcc cacgctgaat       660
tgggaaacag gcaagatcga tcgcttgtgc tttgccgtta tctcgaatga tcctacccett    720
gtaccctctt cagacgaagg ggatattgag aaattccaca actatgcaac taaagcgccg     780
tatgcttatg ttggcgaaaa gcgcacgtta gtgtacggcc ttacgctctc tccgaaagaa     840
gagtactaca aactgggtgc gtattaccac attaccgatg tcctgcgcgg gttactgaaa     900
gcctttgact ctctggagga ttaatga                                         927
```

<210> SEQ ID NO 24
<211> LENGTH: 577
<212> TYPE: PRT
<213> ORGANISM: Bos taurus

<400> SEQUENCE: 24

```
Met Gln Arg Leu Met Lys Phe Arg Val Leu Trp Gly Ile His Met Ser
1               5                   10                  15

Phe Pro Gly Phe His His Ala Pro Gln His Leu Arg Cys Arg Ser Leu
                20                  25                  30

Ser Gly Ala Gly Thr Leu Arg Trp Asn Asp Tyr Asp Arg Pro Glu Glu
            35                  40                  45

Phe Asn Phe Ala Ser Asp Val Leu Asp His Trp Thr Gln Met Glu Lys
        50                  55                  60

Glu Gly Lys Arg Ser Pro Asn Pro Ala Leu Trp Trp Val Asn Asp Gln
65                  70                  75                  80

Gly Asp Glu Val Lys Trp Ser Phe Arg Glu Met Thr Asp Leu Thr Cys
                85                  90                  95

Arg Thr Ala Asn Val Leu Thr Gln Thr Cys Gly Leu Gln Thr Gly Asp
                100                 105                 110

Arg Leu Ala Leu Ile Leu Pro Arg Val Pro Glu Trp Trp Leu Val Cys
            115                 120                 125

Val Gly Cys Ile Arg Thr Gly Ile Ile Phe Met Pro Gly Thr Thr Gln
        130                 135                 140

Met Lys Ala Lys Asp Ile Leu Tyr Arg Leu Gln Val Ser Gly Ala Lys
145                 150                 155                 160

Ala Ile Val Thr Thr Asp Thr Leu Ala Pro Glu Val Glu Ser Val Ala
                165                 170                 175

Pro Glu Cys Pro Ser Leu Lys Thr Lys Leu Leu Val Ser Asp His Ser
                180                 185                 190
```

```
Arg Glu Gly Trp Leu Asp Phe Arg Ser Leu Val Lys Ser Ala Ser Pro
            195                 200                 205

Asp His Ile Cys Ile Lys Ser Lys Thr Leu Asp Pro Met Ala Ile Phe
210                 215                 220

Phe Thr Ser Gly Thr Thr Gly Phe Pro Lys Met Ala Lys His Ser His
225                 230                 235                 240

Gly Phe Ala Leu Arg Ser Tyr Phe Pro Ala Cys Arg Lys Leu Leu Gln
                245                 250                 255

Leu Lys Met Ser Asp Val Phe Trp Cys Leu Ser Asp Thr Gly Trp Ile
            260                 265                 270

Leu Ala Ala Leu Gly Ser Leu Leu Glu Pro Trp Thr Ala Gly Ser Thr
        275                 280                 285

Val Phe Ala His His Leu Pro Gln Phe Asp Pro Lys Val Ile Ile Glu
290                 295                 300

Thr Phe Phe Lys Tyr Pro Ile Thr Gln Cys Leu Ala Ala Pro Ser Val
305                 310                 315                 320

Tyr Arg Met Ile Leu Gln Gln Asn Tyr Thr Ser Leu Arg Phe Pro Thr
                325                 330                 335

Leu Glu His Cys Cys Thr Gly Gly Glu Ala Leu Leu Pro Glu Glu Gln
            340                 345                 350

Glu Gln Trp Lys Arg Gln Thr Gly Val Leu Leu Tyr Gln Ala Tyr Gly
        355                 360                 365

Gln Ser Glu Ala Gly Ile Ser Cys Gly Thr Leu Arg Gly Met Lys Ile
370                 375                 380

Lys Pro Gly Ser Met Gly Lys Ala Ile Pro Pro Phe Asp Ile Gln Ile
385                 390                 395                 400

Ile Asp Asp Lys Gly Asn Ile Gln Pro Pro Asn Thr Glu Gly Asn Ile
                405                 410                 415

Gly Ile Arg Ile Lys Pro Thr Arg Pro Ile Gly Leu Phe Met Tyr Tyr
            420                 425                 430

Glu Asn Asn Pro Glu Lys Thr Ala Glu Val Glu Cys Gly Asp Phe Tyr
        435                 440                 445

Asn Thr Gly Asp Arg Ala Thr Ile Asp Glu Glu Gly Tyr Phe Trp Phe
450                 455                 460

Leu Gly Arg Ser Asp Asp Val Ile Asn Ala Ser Gly Tyr Arg Val Gly
465                 470                 475                 480

Pro Ala Glu Val Glu Asn Ala Leu Ala Glu His Pro Ala Val Ala Glu
                485                 490                 495

Ser Ala Val Val Ser Ser Pro Asp Pro Val Arg Gly Glu Val Val Lys
            500                 505                 510

Ala Phe Ile Val Leu Asn Pro Glu Phe Ser Ser Arg Asp Pro Gly Glu
        515                 520                 525

Leu Thr Lys Glu Leu Gln Gln His Val Lys Ser Val Thr Ala Pro Tyr
530                 535                 540

Lys Tyr Pro Arg Lys Val Glu Phe Val Ser Glu Leu Pro Lys Thr Ile
545                 550                 555                 560

Thr Gly Lys Ile Lys Arg Ser Glu Leu Arg Lys Lys Glu Phe Gly Gln
                565                 570                 575

Lys

<210> SEQ ID NO 25
<211> LENGTH: 566
<212> TYPE: PRT
<213> ORGANISM: Escherichia coli (Stamm K12)
```

<400> SEQUENCE: 25

Met His Pro Thr Gly Pro His Leu Gly Pro Asp Val Leu Phe Arg Glu
1               5                   10                  15

Ser Asn Met Lys Val Thr Leu Thr Phe Asn Glu Gln Arg Arg Ala Ala
            20                  25                  30

Tyr Arg Gln Gln Gly Leu Trp Gly Asp Ala Ser Leu Ala Asp Tyr Trp
                35                  40                  45

Gln Gln Thr Ala Arg Ala Met Pro Asp Lys Ile Ala Val Val Asp Asn
    50                  55                  60

His Gly Ala Ser Tyr Thr Tyr Ser Ala Leu Asp His Ala Ala Ser Cys
65                  70                  75                  80

Leu Ala Asn Trp Met Leu Ala Lys Gly Ile Glu Ser Gly Asp Arg Ile
                85                  90                  95

Ala Phe Gln Leu Pro Gly Trp Cys Glu Phe Thr Val Ile Tyr Leu Ala
            100                 105                 110

Cys Leu Lys Ile Gly Ala Val Ser Val Pro Leu Leu Pro Ser Trp Arg
                115                 120                 125

Glu Ala Glu Leu Val Trp Val Leu Asn Lys Cys Gln Ala Lys Met Phe
130                 135                 140

Phe Ala Pro Thr Leu Phe Lys Gln Thr Arg Pro Val Asp Leu Ile Leu
145                 150                 155                 160

Pro Leu Gln Asn Gln Leu Pro Gln Leu Gln Gln Ile Val Gly Val Asp
                165                 170                 175

Lys Leu Ala Pro Ala Thr Ser Ser Leu Ser Leu Ser Gln Ile Ile Ala
            180                 185                 190

Asp Asn Thr Ser Leu Thr Thr Ala Ile Thr Thr His Gly Asp Glu Leu
        195                 200                 205

Ala Ala Val Leu Phe Thr Ser Gly Thr Glu Gly Leu Pro Lys Gly Val
    210                 215                 220

Met Leu Thr His Asn Asn Ile Leu Ala Ser Glu Arg Ala Tyr Cys Ala
225                 230                 235                 240

Arg Leu Asn Leu Thr Trp Gln Asp Val Phe Met Met Pro Ala Pro Leu
                245                 250                 255

Gly His Ala Thr Gly Phe Leu His Gly Val Thr Ala Pro Phe Leu Ile
            260                 265                 270

Gly Ala Arg Ser Val Leu Leu Asp Ile Phe Thr Pro Asp Ala Cys Leu
        275                 280                 285

Ala Leu Leu Glu Gln Gln Arg Cys Thr Cys Met Leu Gly Ala Thr Pro
    290                 295                 300

Phe Val Tyr Asp Leu Leu Asn Val Leu Glu Lys Gln Pro Ala Asp Leu
305                 310                 315                 320

Ser Ala Leu Arg Phe Phe Leu Cys Gly Gly Thr Thr Ile Pro Lys Lys
                325                 330                 335

Val Ala Arg Glu Cys Gln Gln Arg Gly Ile Lys Leu Leu Ser Val Tyr
            340                 345                 350

Gly Ser Thr Glu Ser Ser Pro His Ala Val Val Asn Leu Asp Asp Pro
        355                 360                 365

Leu Ser Arg Phe Met His Thr Asp Gly Tyr Ala Ala Gly Val Glu
    370                 375                 380

Ile Lys Val Val Asp Asp Ala Arg Lys Thr Leu Pro Pro Gly Cys Glu
385                 390                 395                 400

Gly Glu Glu Ala Ser Arg Gly Pro Asn Val Phe Met Gly Tyr Phe Asp

```
                        405                 410                 415
Glu Pro Glu Leu Thr Ala Arg Ala Leu Asp Glu Glu Gly Trp Tyr Tyr
            420                 425                 430

Ser Gly Asp Leu Cys Arg Met Asp Glu Ala Gly Tyr Ile Lys Ile Thr
            435                 440                 445

Gly Arg Lys Lys Asp Ile Ile Val Arg Gly Gly Glu Asn Ile Ser Ser
            450                 455                 460

Arg Glu Val Glu Asp Ile Leu Leu Gln His Pro Lys Ile His Asp Ala
465                 470                 475                 480

Cys Val Val Ala Met Ser Asp Glu Arg Leu Gly Glu Arg Ser Cys Ala
                485                 490                 495

Tyr Val Val Leu Lys Ala Pro His His Ser Leu Ser Leu Glu Glu Val
            500                 505                 510

Val Ala Phe Phe Ser Arg Lys Arg Val Ala Lys Tyr Lys Tyr Pro Glu
            515                 520                 525

His Ile Val Val Ile Glu Lys Leu Pro Arg Thr Thr Ser Gly Lys Ile
            530                 535                 540

Gln Lys Phe Leu Leu Arg Lys Asp Ile Met Arg Arg Leu Thr Gln Asp
545                 550                 555                 560

Val Cys Glu Glu Ile Glu
                565

<210> SEQ ID NO 26
<211> LENGTH: 744
<212> TYPE: PRT
<213> ORGANISM: Saccharomyces cerevisiae (Stamm CEN.PK113-7D)

<400> SEQUENCE: 26

Met Ala Ala Pro Asp Tyr Ala Leu Thr Asp Leu Ile Glu Ser Asp Pro
1               5                   10                  15

Arg Phe Glu Ser Leu Lys Thr Arg Leu Ala Gly Tyr Thr Lys Gly Ser
                20                  25                  30

Asp Glu Tyr Ile Glu Glu Leu Tyr Ser Gln Leu Pro Leu Thr Ser Tyr
            35                  40                  45

Pro Arg Tyr Lys Thr Phe Leu Lys Lys Gln Ala Val Ala Ile Ser Asn
        50                  55                  60

Pro Asp Asn Glu Ala Gly Phe Ser Ser Ile Tyr Arg Ser Ser Leu Ser
65                  70                  75                  80

Ser Glu Asn Leu Val Ser Cys Val Asp Lys Asn Leu Arg Thr Ala Tyr
                85                  90                  95

Asp His Phe Met Phe Ser Ala Arg Arg Trp Pro Gln Arg Asp Cys Leu
            100                 105                 110

Gly Ser Arg Pro Ile Asp Lys Ala Thr Gly Thr Trp Glu Glu Thr Phe
        115                 120                 125

Arg Phe Glu Ser Tyr Ser Thr Val Ser Lys Arg Cys His Asn Ile Gly
    130                 135                 140

Ser Gly Ile Leu Ser Leu Val Asn Thr Lys Arg Lys Arg Pro Leu Glu
145                 150                 155                 160

Ala Asn Asp Phe Val Val Ala Ile Leu Ser His Asn Asn Pro Glu Trp
                165                 170                 175

Ile Leu Thr Asp Leu Ala Cys Gln Ala Tyr Ser Leu Thr Asn Thr Ala
            180                 185                 190

Leu Tyr Glu Thr Leu Gly Pro Asn Thr Ser Glu Tyr Ile Leu Asn Leu
        195                 200                 205
```

-continued

```
Thr Glu Ala Pro Ile Leu Ile Phe Ala Lys Ser Asn Met Tyr His Val
210                 215                 220
Leu Lys Met Val Pro Asp Met Lys Phe Val Asn Thr Leu Val Cys Met
225                 230                 235                 240
Asp Glu Leu Thr His Asp Glu Leu Arg Met Leu Asn Glu Ser Leu Leu
            245                 250                 255
Pro Val Lys Cys Asn Ser Leu Asn Glu Lys Ile Thr Phe Phe Ser Leu
        260                 265                 270
Glu Gln Val Glu Gln Val Gly Cys Phe Asn Lys Ile Pro Ala Ile Pro
    275                 280                 285
Pro Thr Pro Asp Ser Leu Tyr Thr Ile Ser Phe Thr Ser Gly Thr Thr
290                 295                 300
Gly Leu Pro Lys Gly Val Glu Met Ser His Arg Asn Ile Ala Ser Gly
305                 310                 315                 320
Ile Ala Phe Ala Phe Ser Thr Phe Arg Ile Pro Pro Asp Lys Arg Asn
                325                 330                 335
Gln Gln Leu Tyr Asp Met Cys Phe Leu Pro Leu Ala His Ile Phe Glu
            340                 345                 350
Arg Met Val Ile Ala Tyr Asp Leu Ala Ile Gly Phe Gly Ile Gly Phe
        355                 360                 365
Leu His Lys Pro Asp Pro Thr Val Leu Val Glu Asp Leu Lys Ile Leu
    370                 375                 380
Lys Pro Tyr Ala Val Ala Leu Val Pro Arg Ile Leu Thr Arg Phe Glu
385                 390                 395                 400
Ala Gly Ile Lys Asn Ala Leu Asp Lys Ser Thr Val Gln Arg Asn Val
                405                 410                 415
Ala Asn Thr Ile Leu Asp Ser Lys Ser Ala Arg Phe Thr Ala Arg Gly
            420                 425                 430
Gly Pro Asp Lys Ser Ile Met Asn Phe Leu Val Tyr His Arg Val Leu
        435                 440                 445
Ile Asp Lys Ile Arg Asp Ser Leu Gly Leu Ser Asn Asn Ser Phe Ile
    450                 455                 460
Ile Thr Gly Ser Ala Pro Ile Ser Lys Asp Thr Leu Leu Phe Leu Arg
465                 470                 475                 480
Ser Ala Leu Asp Ile Gly Ile Arg Gln Gly Tyr Gly Leu Thr Glu Thr
                485                 490                 495
Phe Ala Gly Val Cys Leu Ser Glu Pro Phe Glu Lys Asp Val Gly Ser
            500                 505                 510
Cys Gly Ala Ile Gly Ile Ser Ala Glu Cys Arg Leu Lys Ser Val Pro
        515                 520                 525
Glu Met Gly Tyr His Ala Asp Lys Asp Leu Lys Gly Glu Leu Gln Ile
    530                 535                 540
Arg Gly Pro Gln Val Phe Glu Arg Tyr Phe Lys Asn Pro Asn Glu Thr
545                 550                 555                 560
Ser Lys Ala Val Asp Gln Asp Gly Trp Phe Ser Thr Gly Asp Val Ala
                565                 570                 575
Phe Ile Asp Ala Lys Gly Arg Ile Ser Val Ile Asp Arg Val Lys Asn
            580                 585                 590
Phe Phe Lys Leu Ala His Gly Glu Tyr Ile Ala Pro Glu Lys Ile Glu
        595                 600                 605
Asn Ile Tyr Leu Ser Ser Cys Pro Tyr Ile Thr Gln Ile Phe Val Phe
    610                 615                 620
Gly Asp Pro Leu Lys Thr Phe Leu Val Gly Ile Val Gly Val Asp Val
```

-continued

```
625                 630                 635                 640
Asp Ala Ala Gln Pro Ile Leu Ala Ala Lys His Pro Glu Val Lys Thr
                645                 650                 655
Trp Thr Lys Glu Val Leu Val Glu Asn Leu Asn Arg Asn Lys Lys Leu
                660                 665                 670
Arg Lys Glu Phe Leu Asn Lys Ile Asn Lys Cys Ile Asp Gly Leu Gln
                675                 680                 685
Gly Phe Glu Lys Leu His Asn Ile Lys Val Gly Leu Glu Pro Leu Thr
                690                 695                 700
Leu Glu Asp Asp Val Val Thr Pro Thr Phe Lys Ile Lys Arg Ala Lys
705                 710                 715                 720
Ala Ser Lys Phe Phe Lys Asp Thr Leu Asp Gln Leu Tyr Ala Glu Gly
                725                 730                 735
Ser Leu Val Lys Thr Glu Lys Leu
                740
```